United States Patent
Bolognesi et al.

(10) Patent No.: US 7,037,645 B2
(45) Date of Patent: *May 2, 2006

(54) METHODS FOR IDENTIFICATION OF CDS8+ SUPPRESSOR MOLECULES

(75) Inventors: Dani P. Bolognesi, Durham, NC (US); Michael L Greenberg, Durham, NC (US); Simon F Lacey, Azusa, CA (US); Georgia D Tomaras, Durham, NC (US); Kent J. Weinhold, Durham, NC (US)

(73) Assignee: Duke University, Durham, NC (US)

( * ) Notice: Subject to any disclaimer, the term of this patent is extended or adjusted under 35 U.S.C. 154(b) by 403 days.

This patent is subject to a terminal disclaimer.

(21) Appl. No.: 10/071,349

(22) Filed: Feb. 6, 2002

(65) Prior Publication Data

US 2002/0102538 A1 Aug. 1, 2002

Related U.S. Application Data

(63) Continuation of application No. 09/527,320, filed on Mar. 16, 2000, now Pat. No. 6,528,308.

(51) Int. Cl.
*C12Q 1/70* (2006.01)

(52) U.S. Cl. ............... 435/5; 424/188.1; 424/208.1; 424/85.1

(58) Field of Classification Search .............. 435/5; 424/188.1, 208.1, 85.1
See application file for complete search history.

(56) References Cited

U.S. PATENT DOCUMENTS

| | | | |
|---|---|---|---|
| 5,196,524 A | | 3/1993 | Gustafson et al. |
| 5,464,933 A | | 11/1995 | Bolognesi et al. |
| 5,627,023 A | * | 5/1997 | Bolognesi et al. ............. 435/5 |
| 5,656,480 A | | 8/1997 | Wild et al. |
| 5,814,519 A | | 9/1998 | Bolognesi et al. |
| 5,861,490 A | * | 1/1999 | Bolognesi et al. .......... 530/412 |
| 6,586,174 B1 | * | 7/2003 | Bolognesi et al. ............. 435/5 |

FOREIGN PATENT DOCUMENTS

| | | |
|---|---|---|
| WO | WO 94/28920 | 11/1994 |
| WO | WO 96/19495 | 7/1996 |
| WO | WO 99/59615 | 11/1999 |

OTHER PUBLICATIONS

Connor, R. I., et al., 1995, "Vpr is required for efficient replication of human immunodeficiency virus type–1 in mononuclear phagocytes", Virol. 206(2):935–944.*

Jackson, W. H., et al., 1998, "Inhibition of HIV–1 replication by an anti–tat hammerhead ribozyme", Biochem. Biophys. Res. Comm. 245(1):81–84.*

Brinchmann, J. E., et al., 1990, "CD8+ T cells inhibit HIV replication in naturally infected CD4+ T cells", J. Immunol. 144:2961–2966.*

Alkhatib G, Combadiere C, Broder CC, Feng Y, Kennedy PE, Murphy PM, Berger EA, 1996, CC CKR5: a RANTES, MIP–1alpha, MIP–1beta receptor as a fusion cofactor for macrophage–tropic HIV–1, Science Jun. 28;272(5270):1955–1958.

Anderson et al., 1990, A monoclonal antibody reactive with a 15–kDa cytoplasmic granule–associated protein defines subpopulation of CD8+ T lymphocytes, J. Immunol. 144:574–582.

Barker et al., 1995, Effects of $T_H1$ and $T_H2$ cytokines on $CD8^+$ cell response against human immunodeficiency virus: implications for long term survival, Proc. Natl. Acad. Sci. USA 92:11135–11139.

Barré–Sinoussi F et al., 1983, Isolation of a T–lymphotropic retrovirus from a patient at risk for acquired immune deficiency syndrome (AIDS). Science 220:868–871.

Bieniasz PD, Cullen BR, 1998, Chemokine receptors and human immunodeficiency virus infection, Front Biosci. Jan. 1;3:D44–D58.

Bleul CC, Farzan M, Choe H, Parolin C, Clark–Lewis I, Sodroski J, Springer TA, 1996, The lymphocyte chemoattractant SDF–1 is a ligand for LESTR/fusin and blocks HIV–1 entry, Nature Aug. 29; 382(6594):829–833.

Brinchmann J et al., 1991, In vitro replication of HIV–1 in naturally infected $CD4^+$ T cells is inhibited by $rIFN\alpha_2$ and by a soluble factor secreted by activated $CD8^+$ T cells, but not by $rIFN_\beta$, $rIFN_\beta$, $rIFN_\delta$, or recombinant tumor necrosis factor–α, J. Acquired Immune Deficiency Syndrome 4(5):480–488.

Brinchmann J et al., 1989, Reliable isolation of human immunodeficiency virus from cultures of naturally infected $CD4^+$ T cells, J. Virological Methods 25:293–300.

Brinchmann J et al., 1990, $CD8^+$ T cells inhibit HIV replication in naturally $CD4^+$ T cells, evidence for a soluble inhibitor, J. Immunol. 144:2961–2966.

(Continued)

*Primary Examiner*—J. S. Parkin
(74) *Attorney, Agent, or Firm*—Jones Day

(57) ABSTRACT

The present invention relates to a bioactive molecule, herein referred to as the CD8+ suppressor molecule, that is produced by the CD8+ subset of human T-lymphocytes and suppresses type-1 human immunodeficiency virus (HIV-1) replication through inhibition of viral transcription. The invention relates to isolation of CD8+ cell lines and cell clones that produce that antiviral activity and to the development of assay systems for detection of the antiviral activity. The cell lines, cell clones and assay systems, described herein, may be utilized, e.g., to purify, characterize and clone the CD8+ suppressor molecule. The CD8+ suppressor molecule may have therapeutic applications for treatment of diseases associated with HIV-1 infection.

16 Claims, 20 Drawing Sheets

OTHER PUBLICATIONS

Figure 1:
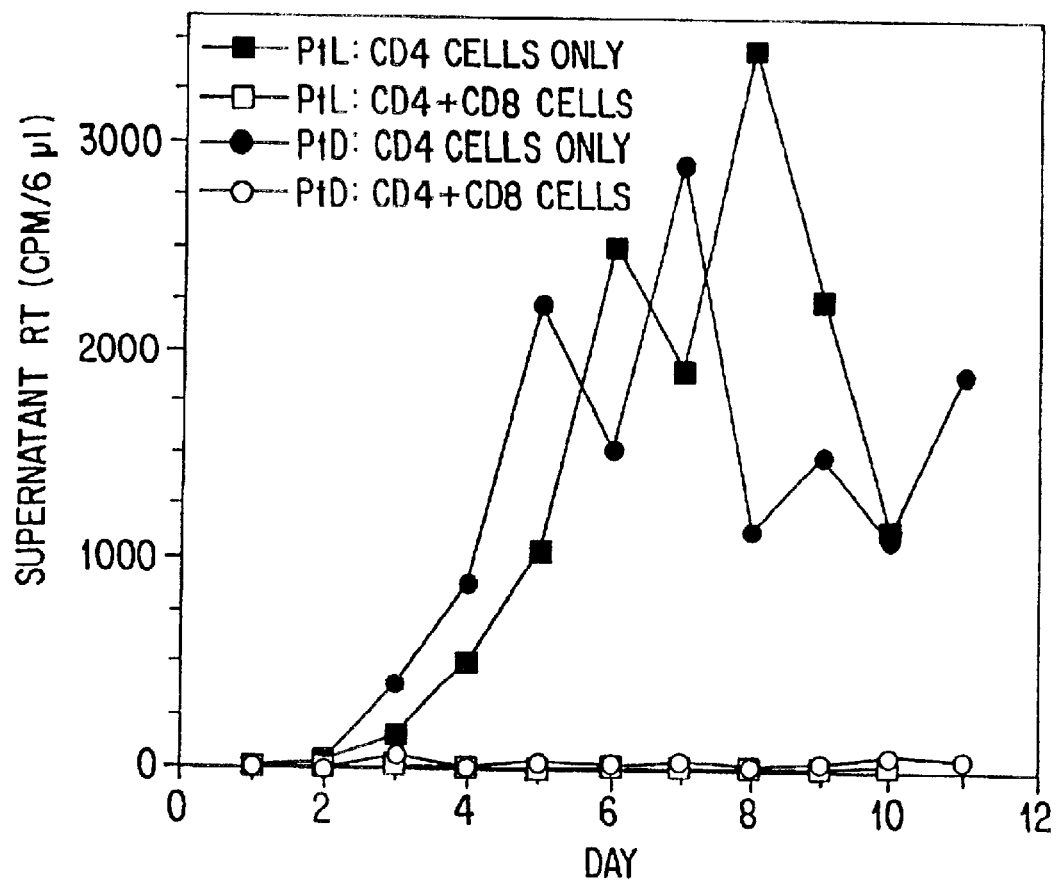

Burgess R. ed., 1987, Protein Purification, Micro to Macro. Alan R. Liss, New York, pp. 17–26.

Cann AJ, ed., 1999, Virus Culture: A Practical Approach. Oxford University Press, New York, pp. 3–4.

Carson K et al., 1994, Companies remain hopeful for vaccines for AIDS despite discouraging results. Gen. Engineering News 14:1,24,34.

Castro B, 1991, Suppression of human immunodeficiency virus replication by $CD8^+$ cells from infected and uninfected chimpanzees. Cellular Immunology 132:246–255.

Chakrabarti S, Brechling K, Moss B, 1985, Vaccinia virus expression vector: coexpression of beta–galactosidase provides visual screening of recombinant virus plaques, Mol Cell Biol. Dec.; 5(12):3403–3409.

Chang T et al., 2002, A soluble factor(s) secreted from CD8+ T lymphocytes inhibits human immunodeficiency virus type 1 replication through STAT1 activation, J. Virology 76(2):569–581.

Chen et al., 1993, $CD8^+$ T lymphocyte–mediated inhibition of HIV–1 long terminal repeat transcription: a novel antiviral mechanism. AIDS Res. Hum. Retroviruses 9:1079–1086.

Chen BK, Saksela K, Andino R, Baltimore D, 1994, Distinct modes of human immunodeficiency virus type 1 proviral latency revealed by superinfection of nonproductively infected cell lines with recombinant luciferase–encoding viruses, J Virol. Feb.;68(2):654–660.

Cocchi F, DeVico AL, Garzino–Demo A, Arya SK, Gallo RC, Lusso P, 1995, Identification of RANTES, MIP–1 alpha, and MIP–1 beta as the major HIV–suppressive factors produced by CD8+ T cells, Science Dec. 15;270(5243):1811–1815.

Cocchi F, DeVico AL, Garzino–Demo A, Cara A, Gallo RC, Lusso P, 1996, The V3 domain of the HIV–1 gp120 envelope glycoprotein is critical for chemokine–mediated blockade of infection, Nat Med. Nov.; 2(11):1244–1247.

Coligan JE et al., 1994, Current Protocols in Immunology, John Wiley & Sons, Inc., 7.19.1–7.21.9.

Connor RI, Chen BK, Choe S, Landau NR, 1995, Vpr is required for efficient replication of human immunodeficiency virus type–1 in mononuclear phagocytes, Virology Feb. 1;206(2):935–944.

Copeland K et al., 1996, $CD8^+$ lymphocyte–mediated suppression of HIV–1 LTR–mediated transcription shows no correlation with clinical stage of disease or health status, XIth Int'l Con. AIDS, Vancouver, Jul. 7–12:12 (Abs. Tu,A, 395).

Cullen B & Greene W, 1989, Regulatory pathways governing HIV replication, Cell 58:423–426.

Dalgleish et al., 1984, The CD4 (T4) antigen is an essential component of the receptor for the AIDS retrovirus, Nature 312:763–767.

Deng H, Liu R, Ellmeier W, Choe S, Unutmaz D, Burkhart M, Di Marzio P, Mamron S, Sutton RE, Hill CM, Davis CB, Peiper SC, Schall TJ, Littman DR, Landau NR, 1996, Identification of a major co–receptor for primary isolates of HIV–1, Nature Jun. 20;381(6584):661–666.

Donzella GA, Schols D, Lin SW, Este JA, Nagashima KA, Maddon PJ, Allaway GP, Sakmar TP, Henson G, De Clercq E, Moore JP, 1998, AMD3100, a small moslecule inhibitor of HIV–1 entry via the CXCR4 co–receptor, Nat Med. Jan. 1998;4(1):72–77.

Dragic T, Litwin V, Allaway GP, Martin SR, Huang Y, Nagashima KA, Cayanan C, Maddon PJ, Koup RA, Moore JP, Paxton WA, HIV–1 entry into CD4+ cells is mediated by the chemokine receptor CC–CKR–5, Nature. Jun. 20, 1996;381(6584):667–673.

Earl PL, Hugin AW, Moss B, 1990, Removal of cryptic poxvirus transcription termination signals from the human immunodeficiency virus type 1 envelope gene enhances expression and immunogenicity of a recombinant vaccinia virus, J Virol. May;64(5):2448–2451.

Endres MJ et al., 1996, CD4–independent infection by HIV–2 is mediated by fusin/CSCR4, Cell Nov. 15; 87(4):745–756.

Fahey JL & Schooley R, 1992, Status of immune–based therapies in HIV infection and AIDS, Clin. Exp. Immunol. 88:1–5.

Flexner C, Broyles SS, Earl P, Chakrabarti S, Moss B, 1988, Characterization of human immunodeficiency virus gag/pol gene products expressed by recombinant vaccinia viruses, Virology Oct. 166(2):339–349.

Fox, 1994, No winners against AIDS, Bio/Technology 12:128.

Gallo et al., 1984, Frequent detection and isolation of cytopathic retroviruses (HTLV–III) from patients with AIDS and at risk for AIDS, Science 224:500–503.

Goff S, Traktman P, Baltimore D, 1981, Isolation and properties of Moloney murine leukemia virus mutants: use of a rapid assay for release of virion reverse transcriptase, J Virol. Apr.;38(1):239–248.

Hara et al. 1991, Subtractive cDNA cloning using oligo(dT)30–latex and PCR: isolation of cDNA clones specific to undifferentiated human embryonal carcinoma cells, Nucleic Acids Dec.;19(25):7097–7104.

Herfort et al. 1991, Simple and efficient subtractive hybridization screening, Biotechniques Nov.;11(5):598, 600, 602–604.

Hsu MC, Schutt AD, Holly M, Slice LW, Sherman MI, Richman DD, Potash MJ, Volsky DJ, 1991, Inhibition of HIV replication in acute and chronic infections in vitro by a Tat antagonist, Science Dec. 20; 254(5039):1799–1802.

Janeway, CA et al., 1999, Immunobiology: The Immune System in Health and Disease. Current Biology Publications, Garland Publishing, London, pp. 231–234.

Jung JU, Trimble JJ, King NW, Biesinger B, Fleckenstein BW, Desrosiers RC, 1991, Identification of transforming genes of subgroup A and C strains of Herpesvirus saimiri, Proc Natl Acad Sci U S A. Aug. 15, 1991;88(16):7051–7055.

Kannagi M, Masuda T, Hattori T, Kanoh T, Nasu K, Yamamoto N, Harada S, 1990, Interference with human immunodeficiency virus (HIV) replication by CD8+ T cells in peripheral blood leukocytes of asymptomtic HIV carriers in vitro, J Virol. Jul.;64(7):3399–3406.

Kannagi M et al., 1988, Suppression of simian immunodeficiency virus replication in vitro by CD8+ lymphocytes, J Immunology 140(7):2237–2242.

Kinter A et al., 1995, Interleukin 2 induces $CD8^+$ T cellmediated suppression of human immunodeficiency virus replication in $CD4^+$ T cells and this effect overrides its ability to stimulate virus expression, Proc. Natl. Acad. Sci. USA 92:10985–10989.

Klatzmann et al., 1984, T–Lymphocyte T4 molecule behaves as the receptor for human retrovirus LAV, Nature 312:767–768.

Kundu S et al., 1992, CD8+ CD11+ suppressor cells in HIV–infected asymptomatic patients: effect on HIV–specific cytotoxicity, Viral Immunol. Spring;5(1):15–25.

Lacey SF, Weinhold KJ, Chen CH, McDanal C, Oei C, Greenberg ML, 1998, *Herpesvirus saimiri* transformation of HIV type 1 suppressive CD8+ lymphocytes from an HIV type 1–infected asymptomatic individual, AIDS Res Hum Retroviruses, Apr. 10, 1998;14(6):521–531.

Lacey SF, McDanal CB, Horuk R, Greenberg ML, 1997, The CXC chemokine stromal cell–derived factor 1 is not responsible for CD8+ T cell suppression of syncytia–inducing strains of HIV–1, Proc Ntl Acad Sci U S A. Sep. 2;94(18):9482–9847.

Lacey SF et al., 1994, *Herpesvirus saimiri* transformation of suppressive $CD8^+$ T–lymphocytes from a $HIV^+$ asymptomatic patient, AIDS Res. and Human Retroviruses 10(Suppl. 3):S70.

Levy J et al., 1994, Mechanism of $CD8^+$ cell suppression of HIV replication, J. Cell. Biochem. Suppl. 18B:111.

Mackewicz C et al., 1991, $CD8^+$ lymphocytes from HIV–1 seropositive individuals block HIV replication in $CD4^+$ lymphocytes by inhibiting viral RNA synthesis. Int. Conf. AIDS 7:74.

Mackewicz C et al., 1991, $CD8^+$ cell anti–HIV activity correlates with the clinical state of the infected individual J. Clin. Invest. 87:1462–1466.

Mackewicz C et al., 1992, $CD8^+$ cell anti–HIV activity: non–lytic suppression of virus replication. AIDS Res. Human Retroviruses 8:1039–1050.

Maddon et al., 1986, The T4 gene encodes the AIDS virus receptor and is expressed in the immune system and the brain, Cell 47:333–348.

Malim et al., 1988, Immunodeficiency virus rev trans–activator modulates the expression of the viral regulatory genes, Nature 335:181–183.

Moore JP, Trkola A, Dragic T, 1997, Co–receptors for HIV–1 entry, Curr Opin Immunol. Aug;9(4):551–562.

Oberlin E, Amara A, Bachelerie F, Bessia C, Virelizier JL, Arenzana–Seisdedos F, Schwartz O, Heard JM, Clark–Lewis I, Legler DF, Loetscher M, Baggiolini M, Moser B, 1996, The CXC chemokine SDF–1 is the ligand for LESTR/fusin and prevents infection by T–cell–line–adapted HIV–1, Nature Aug. 29; 382(6594):833–835.

Old R et al., 1989, Principles of Gene Manipulation, an Introduction to Genetic Engineering. Blackwell Scientific Publications, Oxford. pp. 137–139.

Pantaleo et al., 1992, Defective clonogenic potential of $CD8^+$ T lymphocytes in patients with AIDS. expansion in vivo of nonclonogenic $CD3^+$ $CD8^+$ $DR^+$ $CD25^-$ T Cell Population, J Immunol. 144:1702.

Powell J et al., 1990, $CD8^+$ T cell–induced inhibition of retroviral replication is mediated at the transcriptional level, Sym. nonhuman primate models AIDS 8:43.

Powell J et al., 1991, Regulation of immune activation/retroviral replication by $CD8^+$ T cells, Ann. N.Y. Acad. Sci. USA 636:360–363.

Powell J et al., 1993, Inhibition of cellular activation of retroviral replication by $CD8^+$ T cells derived from non–human primates, Clin. Exp. Immunol. 91:473–481.

Srivastava KK, Fernandez–Larson R, Zinkus DM, Robinson HL, 1991, Human immunodeficiency virus type 1 NL4–3 replication in four T–cell lines: rate and efficiency of entry, a major determinant of permissiveness, J Virol. Jul.;65(7):3900–3902.

Stein D et al., 1993, Immune–based therapeutics: scientific rationale and the promising approaches to the treatment of the human immunodeficiency virus–infected individual, Clin. Infect. Dis. 17:749–771.

Teich et al., 1984, Pathogenesis of lentivirus, in RNA Tumor Viruses, Weiss et al., eds., CSH Press, pp. 949–956.

Tomaras G & Greenberg M, 2001, $CD8^+$ T cell mediated noncytolytic inhibition of human immunodeficiency virus type 1, Front. Biosci. 6:D575–598.

Tomaras G & Greenberg M, 2001, Mechanisms for HIV–1 entry: current strategies to interfere with this step, Curr Infect Dis Rep. Feb. 2001;3(1):93–99.

Tomaras G et al., 2000, $CD8^+$ T cell–mediated suppressive activity inhibits HIV–1 after virus entry with kinetics indicating effects on virus gene expression, Proc Natl Acad Sci U S A. Mar. 28;97(7):3503–3508.

Tsubota H et al., 1989, $CD8^+$ lymphocyte lines can harbor the AIDS virus in vitro, J Immuology 143(3):858–863.

Tsubota H et al., 1989, A cytotoxic T lymphocyte inhibits acquired immunodeficiency syndrome virus replication in peripheral blood lymphocytes, J Exp. Med. 169:1421–1434.

Walker et al., 1986, $CD8^+$ lymphocytes can control HIV infection in vitro by suppressing virus replication. Science 234:1563–1566.

Walker C & Levy J, 1989, A diffusible lymphokine produced by $CD8^+$ T lymphocytes suppresses HIV replication, Immunology 66:628–630.

Walker CM, Erickson AL, Hsueh FC, Levy JA, 1991, Inhibition of human immunodeficiency virus replication in acutely infected CD4+ cells by CD8+ cells involves a noncytotoxic mechanism, J Virol. Nov. 1991; 65(11):5921–5927.

Walker C et al., 1989; $CD8^+$ T lymphocyte control of HIV replication in cultured $CD4^+$ cells varies among infected individuals, Cellular Immunology 119:470–475.

Walker C et al., 1991, $CD8^+$ cells from HIV–1–infected individuals inhibit acute infection by human and primate immunodeficiency viruses, Cellular Immunology 137:420–428.

Wild C, Greenwell T, Matthews T, 1993, A synthetic peptide from HIV–1 gp41 is a potent inhibitor of virus–mediated cell–cell fusion, AIDS Res Hum Retoviruses, Nov.;9(11):1051–1053.

Willey RL, Smith DH, Lasky LA, Theodore TS, Earl PL, Moss B, Capon DJ, Martin MA, 1988, In vitro mutagenesis identifies a region within the envelope gene of the human immunodeficiency virus that is critical for infectivity, J Virol. Jan;62(1):129–147.

Wiviott L. et al., 1990, $CD8^+$ lymphocytes suppress HIV production by autologous $CD4^+$ cells without eliminating the infected cells from culture, Cellular Immunology 128:628–634.

Wong–Staal F & Gallo R, 1985, Human T–lymphotropic retroviruses, Nature 317:395–403.

Zhang L et al., 2002, Contribution of human α–defensin–1, –2, and –3 to the anti–HIV–1 activity of CD8 antiviral factor, Science 298(5595):995–1000.

* cited by examiner

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: PCR Primer for HVS dihydrofolate reductase gene

<400> SEQUENCE: 1
gagagctcaa aatcataact agct                                           24

<210> SEQ ID NO 2
<211> LENGTH: 29
<212> TYPE: DNA
<213> ORGANISM: Artificial Sequence
<220> FEATURE:
<223> OTHER INFORMATION: PCR Primer for HVS dihydrofolate reductase gene

<400> SEQUENCE: 2
ggttcttttg ctaaactgta ttgttgctg                                      29

<210> SEQ ID NO 3
<211> LENGTH: 30
<212> TYPE: DNA
<213> ORGANISM: Artificial Sequence
<220> FEATURE:
<223> OTHER INFORMATION: PCR Primer for HVS ORF2  gene

<400> SEQUENCE: 3
agttccacac aactaactac tagatgagat                                     30

<210> SEQ ID NO 4
<211> LENGTH: 30
<212> TYPE: DNA
<213> ORGANISM: Artificial Sequence
<220> FEATURE:
<223> OTHER INFORMATION: PCR Primer from HVS dihydrofolate reductase gene

<400> SEQUENCE: 4
atggcaagcg aaccgaacct aagatatcca                                     30
```

METHODS FOR IDENTIFICATION OF CDS8+ SUPPRESSOR MOLECULES

This is a continuation of application Ser. No. 09/527,320, filed Mar. 16, 2000, now U.S. Pat. No. 6,528,308, which is incorporated herein by reference in its entirety.

1. INTRODUCTION

The present invention relates to bioactive molecules, herein referred to as $CD8^+$ suppressor molecules, that are produced by the $CD8^+$ subset of human T-lymphocytes and suppress human immunodeficiency virus (HIV) replication through inhibition of viral transcription. The invention relates to isolation of clonal $CD8^+$ cell lines and/or the generation of permanently established transformed $CD8^+$ cell lines that produce antiviral activity. The invention also relates to the development of assay systems for detection of the antiviral activity. The cell lines and assay systems, described herein, may be utilized, e.g., to purify, characterize and clone a $CD8^+$ suppressor molecule. The $CD8^+$ suppressor molecules may be used, e.g., in therapeutic applications for treatment of diseases associated with HIV infection.

2. BACKGROUND OF THE INVENTION

The type-1 human immunodeficiency virus (HIV-1) has been implicated as the primary cause of the slowly degenerate disease of the immune system termed acquired immune deficiency syndrome (AIDS) (Barré-Sinoussi, F. et al., 1983 Science 220:868–70; Gallo, R. et al. 1984, Science 224:500–3). Infection of the $CD4^+$ subclass of T-lymphocytes with the HIV-1 virus leads to depletion of this essential lymphocyte subclass which inevitably leads to opportunistic infections, neurological disease, neoplastic growth and eventually death. HIV-1 infection and HIV-1 associated diseases represent a major health problem and considerable attention is currently being directed towards the successful design of effective therapeutics.

HIV-1 is a member of the lentivirus family of retroviruses (Teich, N. et al., 1984 In RNA Tumor Viruses ed. R. Weiss, N. Teich, H. Varmus, J. Coffin CSH Press, pp. 949–56). The life cycle of HIV-1 is characterized by a period of proviral latency followed by active replication of the virus. The primary cellular target for the infectious HIV-1 virus is the $CD4^+$ subset of human T-lymphocytes. Targeting of the virus to the $CD4^+$ subset of cells is due to the fact that the $CD4^+$ cell surface protein acts as the cellular receptor for the HIV-1 virus (Dalgleish, A. et al., 1984, Nature 312:763–67; Klatzmann et al. 1984, Nature 312:767–68; Maddon et al. 1986 Cell 47:333–48).

In more detail, HIV-1 infection of susceptible cells is initiated via interactions between the virus envelope glycoprotein (gp120) and the $CD4^+$ cell surface receptor. Fusion of the viral and cell membranes then proceeds through subsequent interaction of this complex with a specific chemokine receptor, primarily the CCR5 or the CXCR4 chemokine receptor (Bieniasz & Cullen, 1998, Front. Biosci. 3:D44–D58; Moore et al., 1997, Curr. Opin. Immunol. 9:551–562). HIV-1 isolates that can infect T-cell lines and induce syncytia (SI) use the CXCR4 receptor and are termed X4 HIV-1. Such isolates are typically recovered late in the course of HIV progression and differ from the non-syncytia inducing (NSI) strains which predominate in the early stages of HIV infection. NSI strains gain entry to target cells through use of the CCR5 receptor and are referred to as R5 HIV-1.

After binding to the cell surface and fusion of the virus and cell membrane, the HIV-1 virion becomes internalized and the virus's RNA genome is converted into linear double-stranded DNA molecules. This process is dependent on the action of the virally encoded reverse transcriptase. Following replication of the viral genome, the linear DNA molecule integrates into the host genome through the action of the viral integrase protein, thus establishing the proviral form of HIV-1. During the early phase of proviral expression, transcription of the viral genome results in expression of regulatory proteins such as Tat, Nef and Rev. Transcriptional activation of the proviral DNA is mediated through the viral 5' LTR sequences (long terminal repeats). The initial low level of viral transcription is dramatically increased by the HIV encoded transactivator protein termed tat (transactivator protein) (Cullen, B. R. et al. 1989, Cell 58:423–26). The Rev protein promotes the transition from the early phase expression of regulatory proteins to late phase expression of structural proteins. Assembly of newly synthesized viral particles is followed by budding of virus particles from the cell membrane allowing the virus to infect new cells.

The HIV-1 virus is capable of establishing a latent state of infection for prolonged periods of time. Individuals infected with the human immunodeficiency virus may remain clinically healthy for long periods of time, with the estimated average length of the asymptomatic period between primary HIV infection and the progression to AIDS and increase in viral replication being approximately 8 to 10 years. It is generally believed that the humoral immune response to HIV-1 is not sufficiently protective against progression of the disease. Therefore, attention has turned to the possibility that the T-lymphocyte population of cells may maintain the period of latency by directly inhibiting HIV-1 replication.

A number of groups have recently noted that the $CD8^+$ subset of T-lymphocytes have the ability to inhibit the replication of HIV-1 in vitro (Walker, C. M. et al., 1989, Cellular Immunology 119:470–475; Kannagi, M. et al. 1990, J. Virology 64:3399–3406; Walker, C. M. et al., 1991 J. Virology 65:5921–5927). For example, addition of $CD8^+$ cells to naturally HIV-1 infected $CD4^+$ cell cultures has been found to inhibit the replication of HIV-1 in the infected cultures in a dose dependent manner. (Ref. supra). Furthermore, the inhibitory effect is not entirely dependent on cell-cell contact as an inhibitory effect is observed across a semi-permeable membrane suggesting that at least a portion of the $CD8^+$ suppressor activity is due to a soluble inhibitor of HIV-1 replication. (Ref. supra). To date, the molecular identity of the $CD8^+$ suppressor molecule, or a combination of factors, as well as the mechanism by which it exerts its antiviral effect remains undefined.

Because such $CD8^+$ suppressor molecules would be useful, e.g., in the treatment and/or inhibition of HIV infection, there is a need in the art to identify and characterize such molecules and their HIV suppression activity. There is also a need for methods, particularly screening methods, which may be used, e.g., to screen $CD8^+$ cells for such suppression activity and to isolate such $CD8^+$ suppressor molecules.

3. SUMMARY OF THE INVENTION

The present invention relates to molecules produced by the $CD8^+$ subclass of T-lymphocytes that are able to inhibit HIV viral replication. The molecules can be e.g., soluble molecules produced and/or secreted by the $CD8^+$ subclass of T-lymphocytes or alternatively, can be expressed on the surface of a CD8+ lymphocyte. The invention further relates to the observation that the mechanism by which the suppressor molecule exerts its antiviral activity is at the level of inhibition of viral gene expression from the viral LTR promoter.

The invention also relates to and is based, at least in part, on the discovery that the antiviral activity of a CD8+ suppressor molecule occurs at a stage or stages of the viral replication cycle after viral entry into CD4+ cells and before the stages of expression of late gene products, viral assembly, maturation and budding. For example, the Example presented in Section 10, below, presents data, for the first time, demonstrating that CD8+ suppressor activity occurs during a stage of the viral replication cycle such as integration of viral DNA, transactivation from the proviral state, export of tat and/or rev into the cytoplasm and then back into the nucleus and/or tat mediated enhancement of transcription.

In a principle embodiment, the invention is directed to an assay system that can be used for detection of HIV inhibitory activity during a single cycle of HIV infection. In particular, the invention provides a single cycle HIV-1 reporter vector wherein a reporter gene is operatively associated with an HIV-1 promoter. In preferred embodiments of the invention, the reporter gene is expressed during the early proviral gene expression stage of the viral replication cycle. For example, in a particularly preferred embodiment described herein, the reporter gene is expressed in place of one or more early proviral genes, such as in place of the HIV-1 nef gene.

In such an assay system, the presence of a suppressor molecule can be detected by measuring the levels of the reporter gene product. Such an assay system can also be used to identify the stage in the proviral replication cycle targeted by the suppressor molecule. Thus, the assay system enables a user to both detect a suppressor molecule and characterize its activity.

Using such a pseudotyped virus screening assay a user can readily screen for and detect suppressor compounds, including CD8+ suppressor compounds, that inhibit HIV replication during a particular stage or particular stages of the HIV replication cycle. For example, compounds can be detected and/or identified which inhibit HIV by targeting the stage of viral entry, the stage of reverse transcription or the stage of early viral gene expression, to name a few. The method simply involves contacting a host cell with a single cycle HIV pseudotyped virus of the invention followed by contacting the host cell with a test compound. HIV inhibition is then ascertained by detecting inhibition of reporter gene activity. An HIV suppressor compound will inhibit a single cycle of HIV replication as long as it is contacted to the host cell prior to a time interval when the stage of the pseudotyped virus replication cycle targeted by the compound is complete (i.e., after viral entry, after reverse transcription or after expression of early viral genes).

The invention also provides an assay system, which is also described in U.S. Pat. Nos. 5,627,023 and 5,861,490 (filed on Mar. 29, 1993 and Jun. 6, 1995, respectively) to be used for detection of the HIV inhibitory activity, whereby the HIV LTR sequence is cloned adjacent to a reporter gene such as the CAT gene. In such an assay system, the presence of the suppressor molecule may be determined by measuring the levels of reporter gene product.

The present invention further relates to the isolation and characterization of CD8+ cell clones that produce the antiviral activity, e.g., using one or more of the screening assays of the invention. The invention also relates to the generation of permanently established CD8+ cell lines that produce the antiviral activity. The antiviral activity produced by such cell lines may be produced by a soluble, cytolytic molecule produced by said cell lines or, alternatively, may be produced by a non-cytolytic molecule produced by said cell lines (e.g., a molecule expressed on the membrane of said cell lines). Such cell lines may be generated by transferring cellular or viral genes capable of transformation or immortalization into CD8+ cells. Exemplary cell lines which are considered part of the present invention include the cell lines described hereinbelow, which referred to as DU-JR.HVS and DU.HS-HVS and identified by the ATCC Accession Nos. (PTA-1551 and PTA1552, respectively).

CD8+ clonal cells and/or CD8+ permanently established cell lines that produce the antiviral activity of interest may be advantageously used for large scale isolation and characterization of the suppressor molecule and/or as a source of mRNA for construction of cDNA libraries that may be used for cloning the suppressor molecule. The invention also relates to the use of the suppressor molecule in the treatment of HIV-infection.

4. BRIEF DESCRIPTION OF THE FIGURES

FIG. 1. CD8+ Cells from HIV-1 Seropositive Individuals Suppresses virus production.

Figure 2:
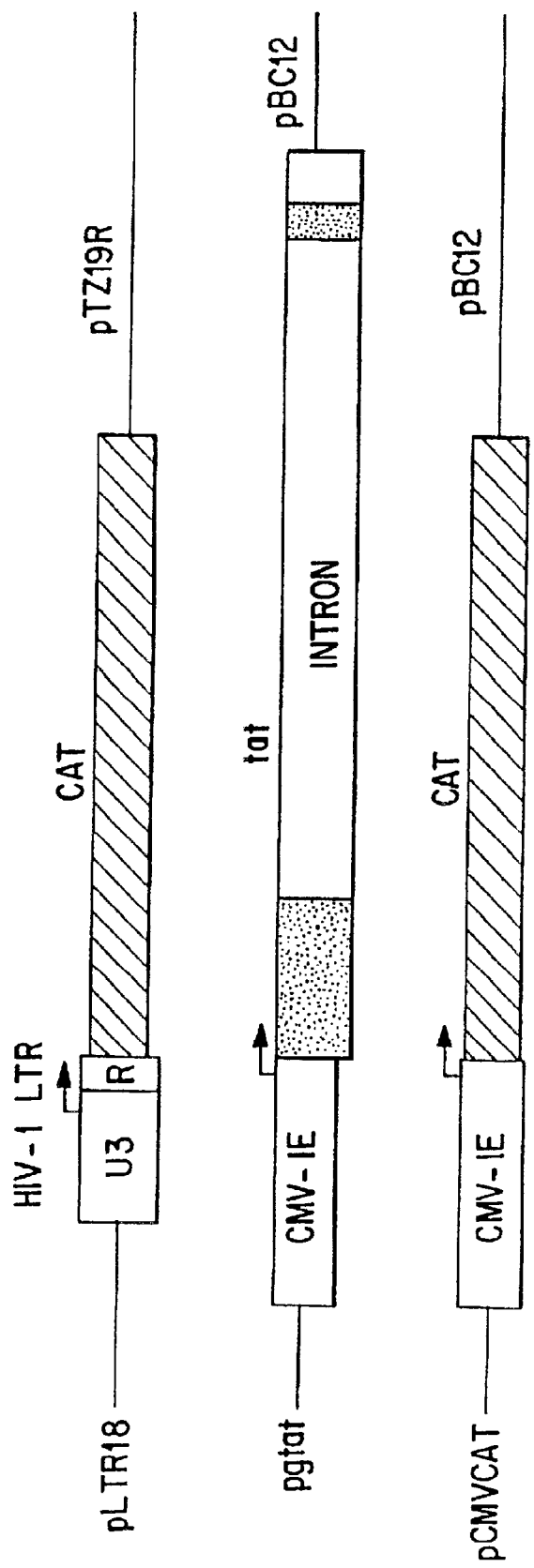

FIG. 2. Plasmid constructs used in HIV-1 LTR transcription assays.

Figure 3:
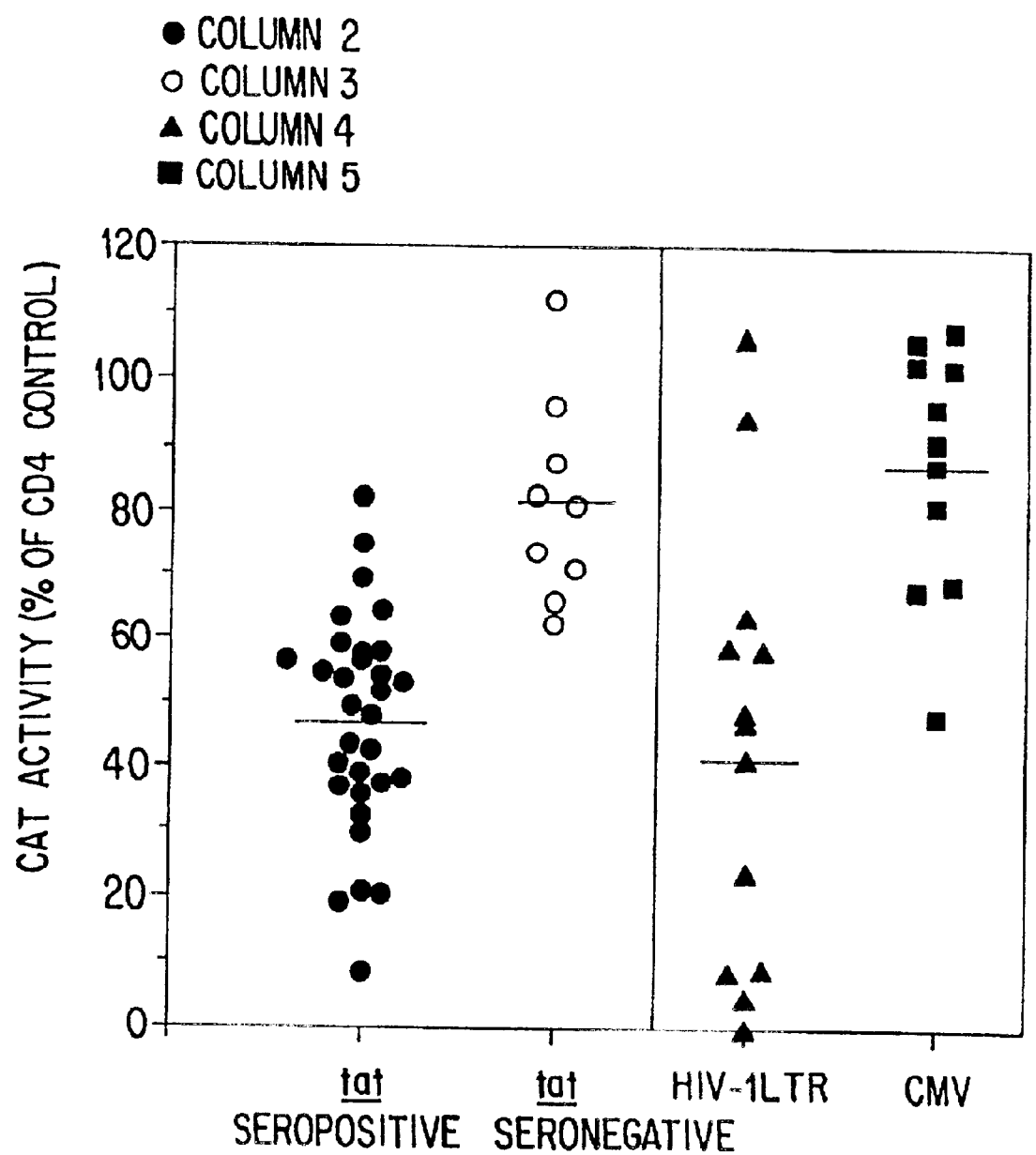

FIG. 3. CD8+ Cells from HIV-1 infected individuals suppress HIV-1 LTR transcription. Data are plotted for CAT activity in cultures containing autologous CD8+ cells compared to the activity measured in cultures derived from the same transfection containing autologous CD4+ cells. Horizontal lines are drawn to indicate the means of each population.

Figure 4:
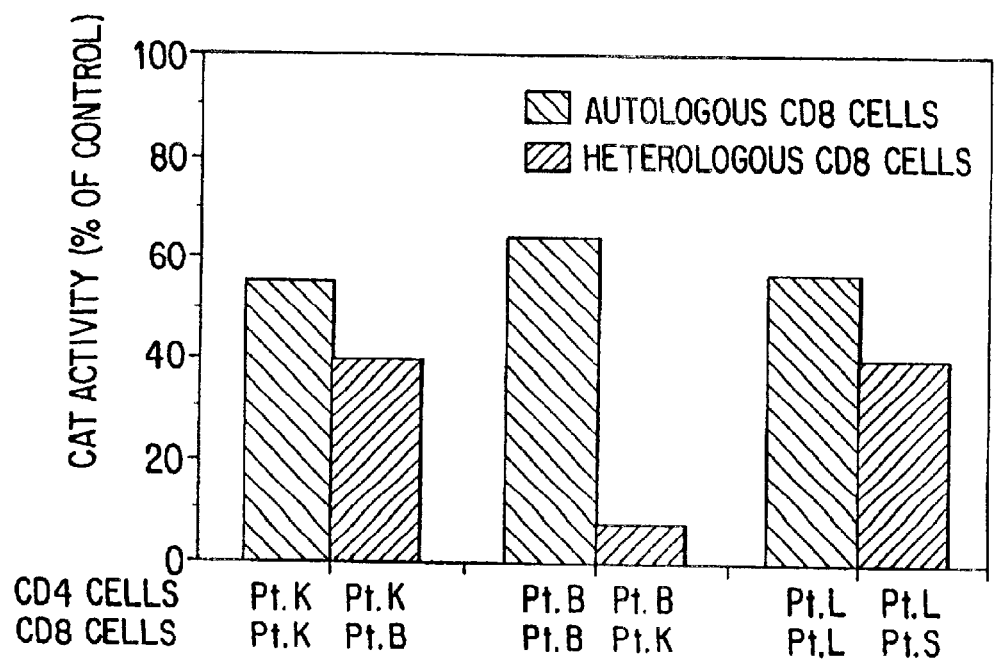

FIG. 4. CD8+ cells suppress Tat-mediated transcription in heterologous CD4+ cells. Data are plotted for CAT activity in cultures containing autologous or heterologous CD8+ cells compared to the activity measured in cultures derived from the same transfection containing autologous CD4+ cells.

Figure 5:
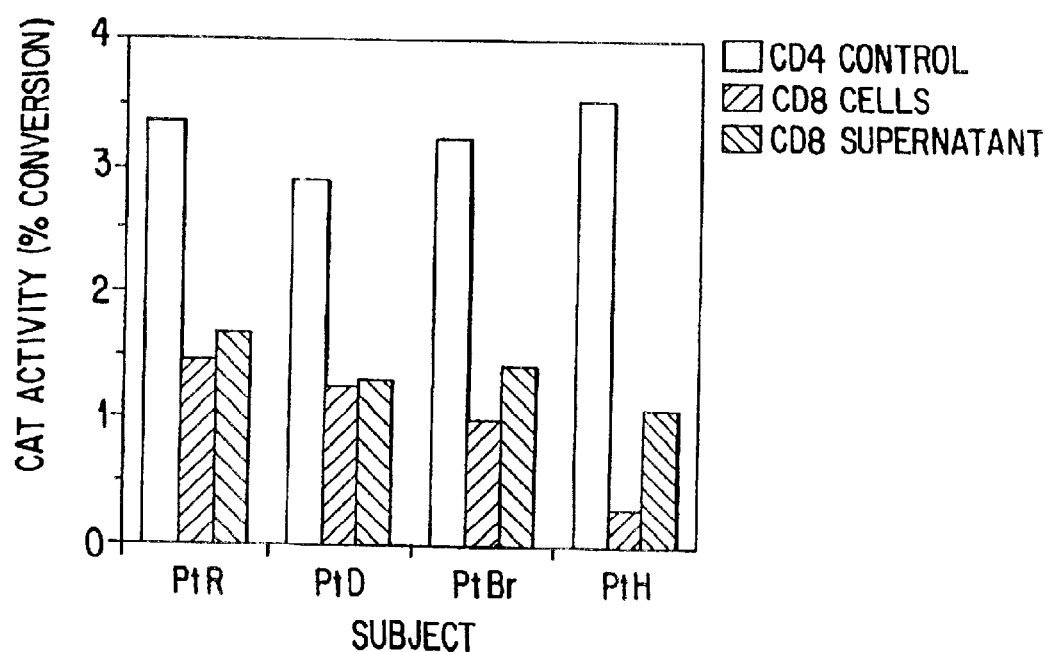

FIG. 5. A soluble factor from CD8+ cells inhibits Tat-mediated transcription. CAT activity was measured in cultures containing autologous CD4+ cells, cultures containing autologous CD8+ cells and cultures containing autologous CD8+ cell conditioned medium. Each data set from an individual subject was derived from a single transfection. CAT activity is expressed as percent conversion, each assay was based on $5 \times 10^6$ transfected CD4+ cells.

Figure 6:
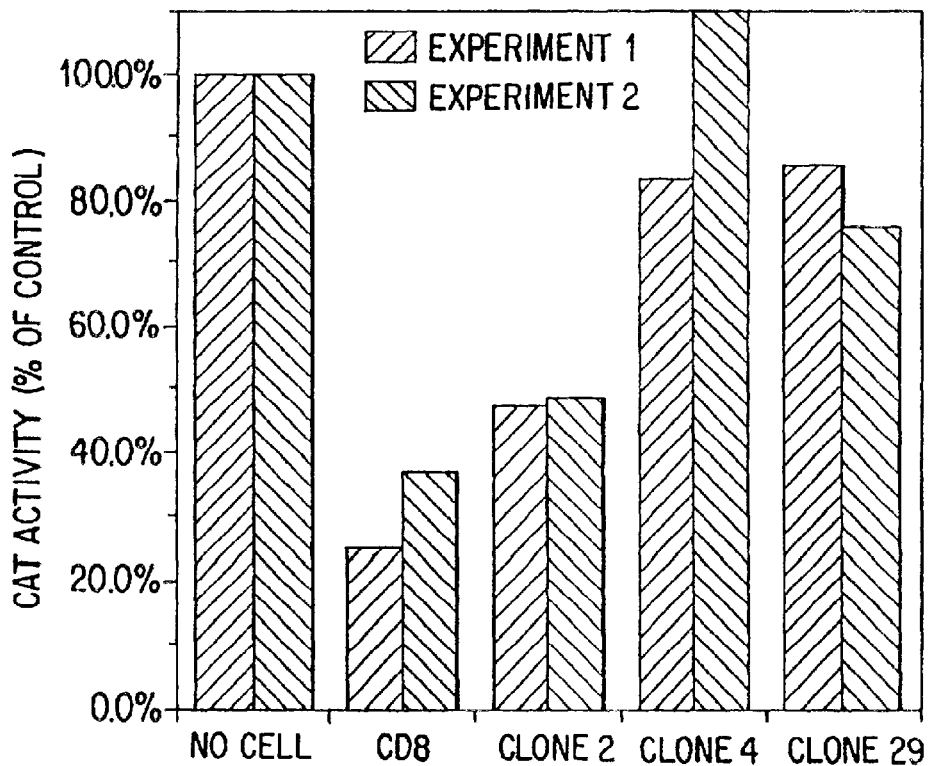

FIG. 6. HIV transcriptional inhibition is expressed by a primary CD8+ cell clone.

Figure 7A:
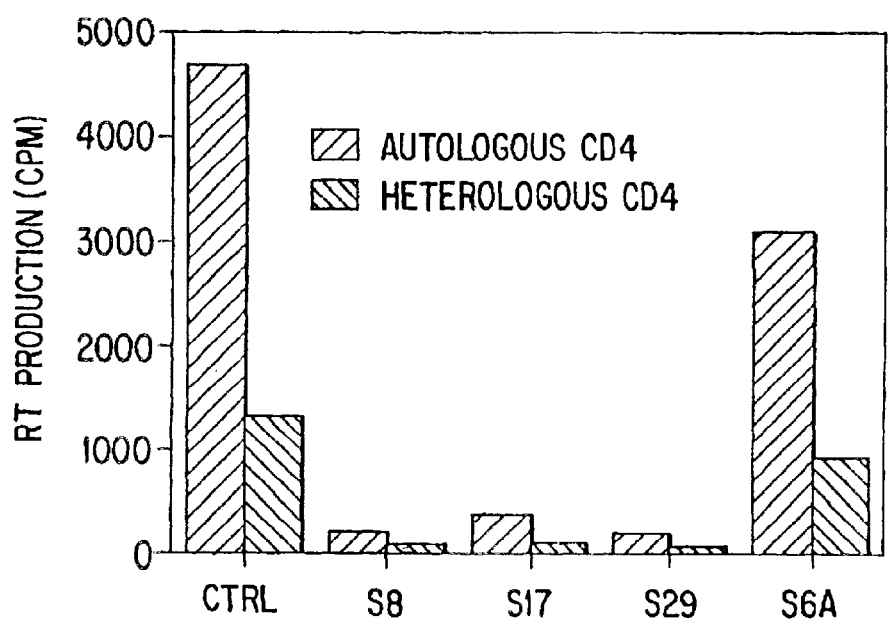
Figure 7B:
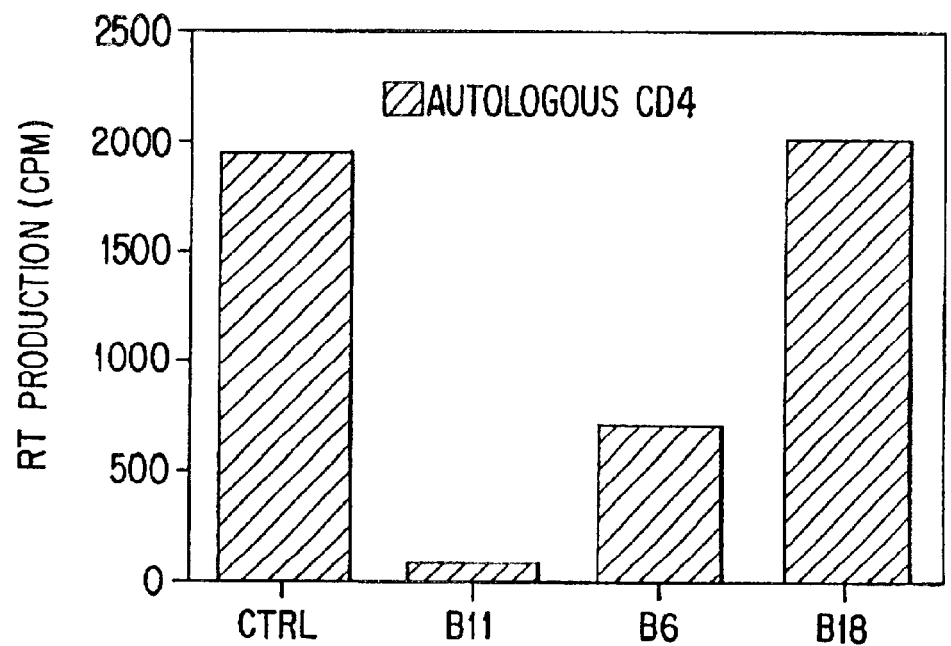
Figure 7C:
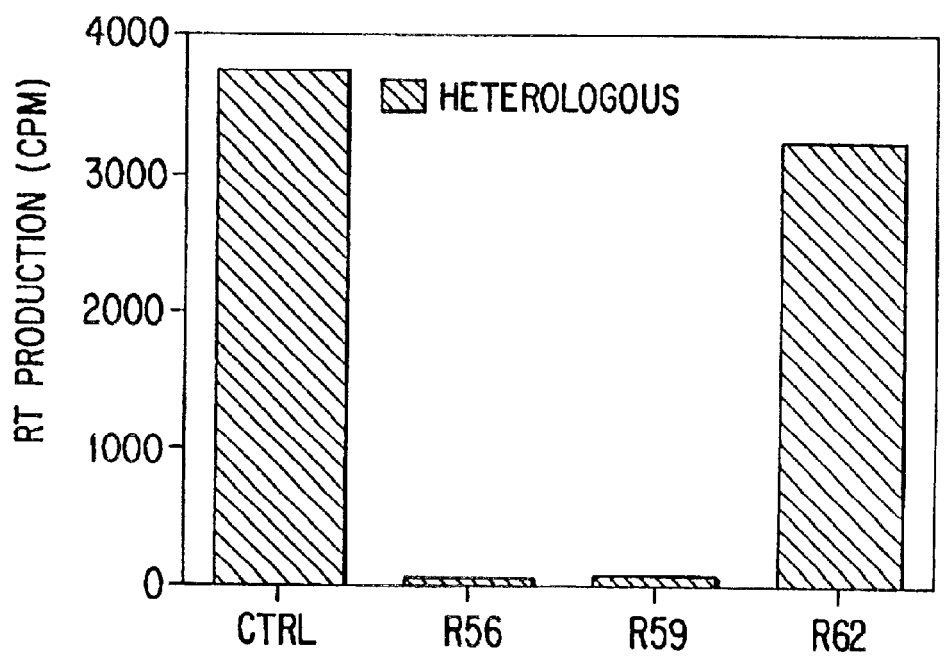

FIG. 7. Anti-HIV-1 activity of CD8+ clones in autologous and heterologous co-culture screening assays. Controls represent RT production of infected CD4+ cells in the absence of other cells. (A) Clones from patient S were screened against both heterologous, acutely infected CD4+ cells and autologous, naturally infected CD4+ cells. The data shown was collected on day 6 of assay. (B) Clones from patient B were screened against autologous, naturally infected CD4+ cells. Data shown was also collected on day 6. (C) Clones from patient R were screened against heterologous, naturally infected CD4+ cells. Data shown was collected on day 3 of assay.

Figure 8:
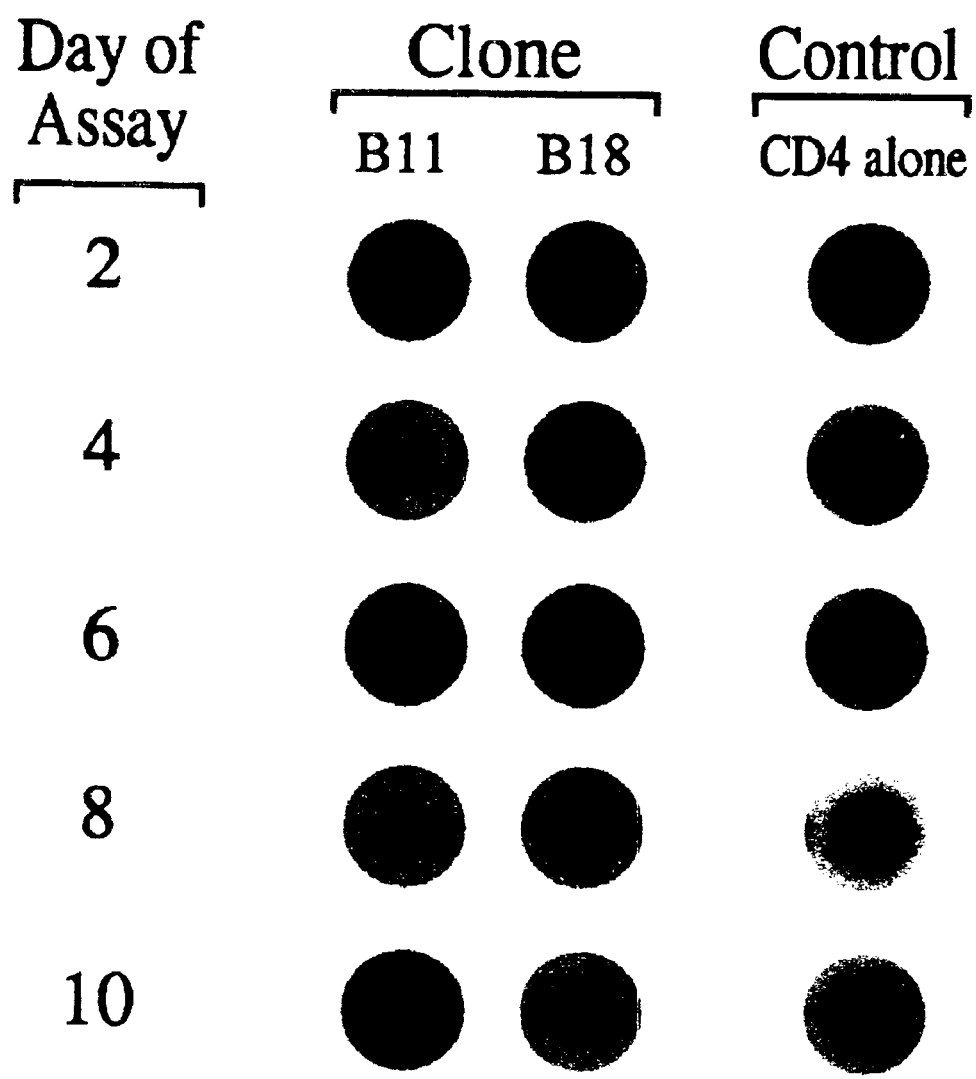

FIG. 8. Autoradiograph of RT assay showing anti-HIV-1 activity of clone B11 compared to non-active clone B18 and to acutely infected CD4+ cells alone. The E:T ratio at the commencement of the assay was 2:1.

Figure 9A:
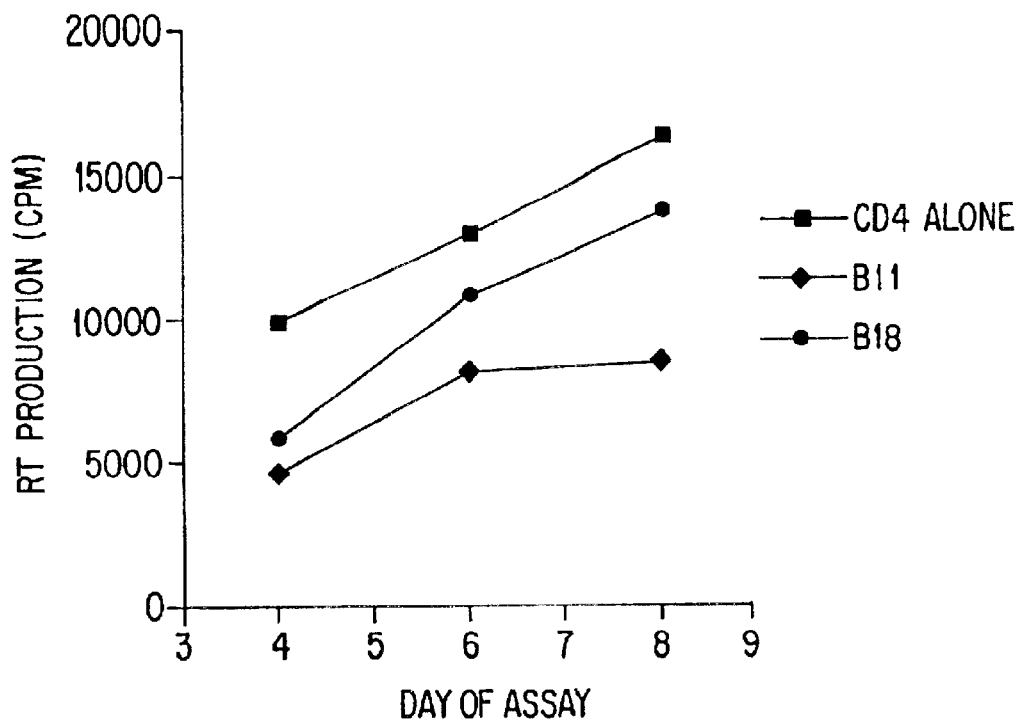
Figure 9B:
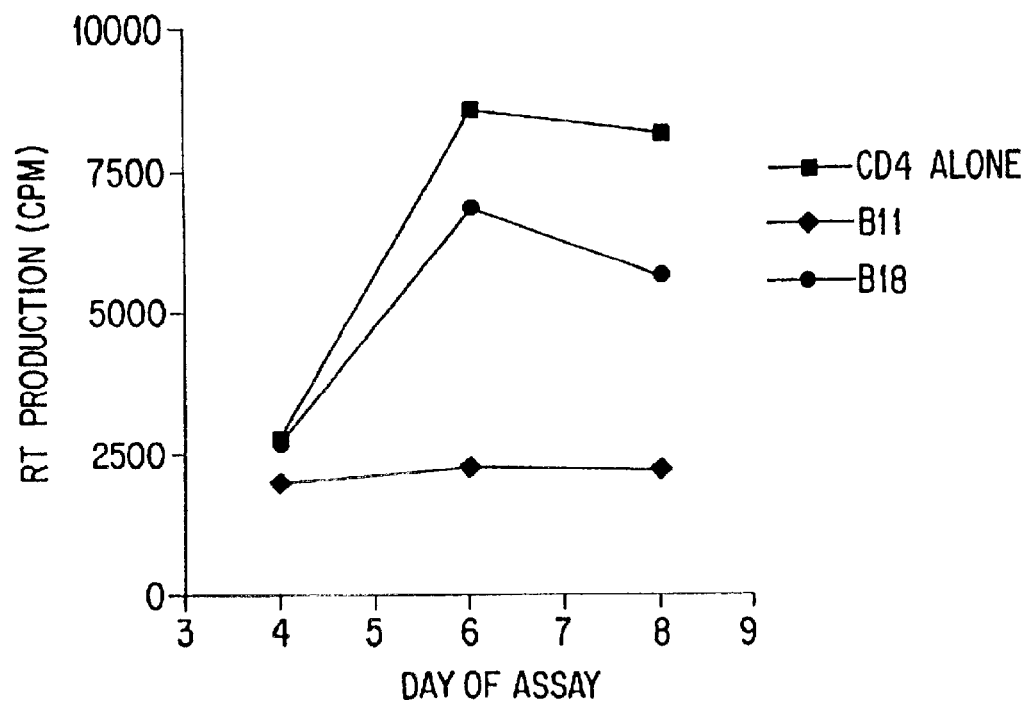

FIG. 9. CD8+ clones from Patient B were separated from acutely infected CD4+ targets by a filter with 0.4 μm pores in the context of transwell plates (Costar). A 4:1 E:T ratio was employed. Supernatant was sampled for RT activity at day 4, 6, and 8 after culture as shown. The second graph shows the results of a parallel coculture experiment. A 2:1 E:T ratio was employed. The effectors of both experiments originated from the same stock culture.

Figure 10:
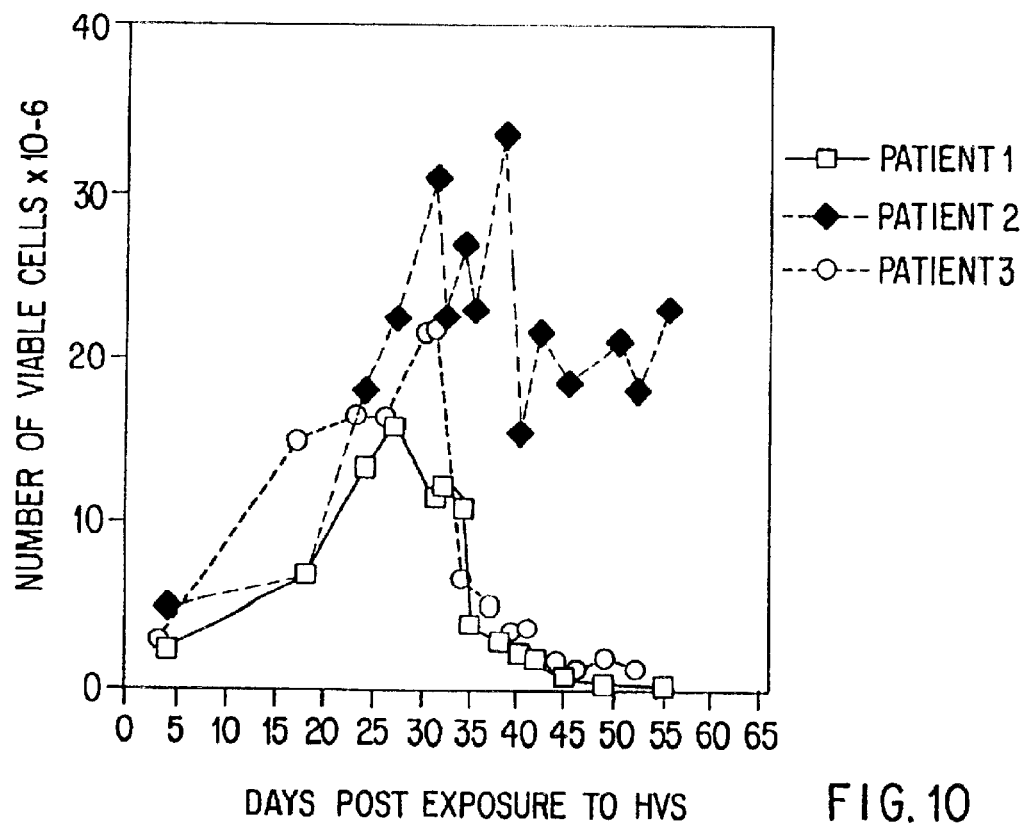

FIG. 10. Establishment of a HVS-transformed CD8+ population. CD8+ cells from three HIV+ patients 1(□), 2(◆), and 3(○) were exposed to HVS at day 0. Viable cell numbers as measured by erythrosin red dye exclusion are shown over the course of 57 days.

Figure 11:
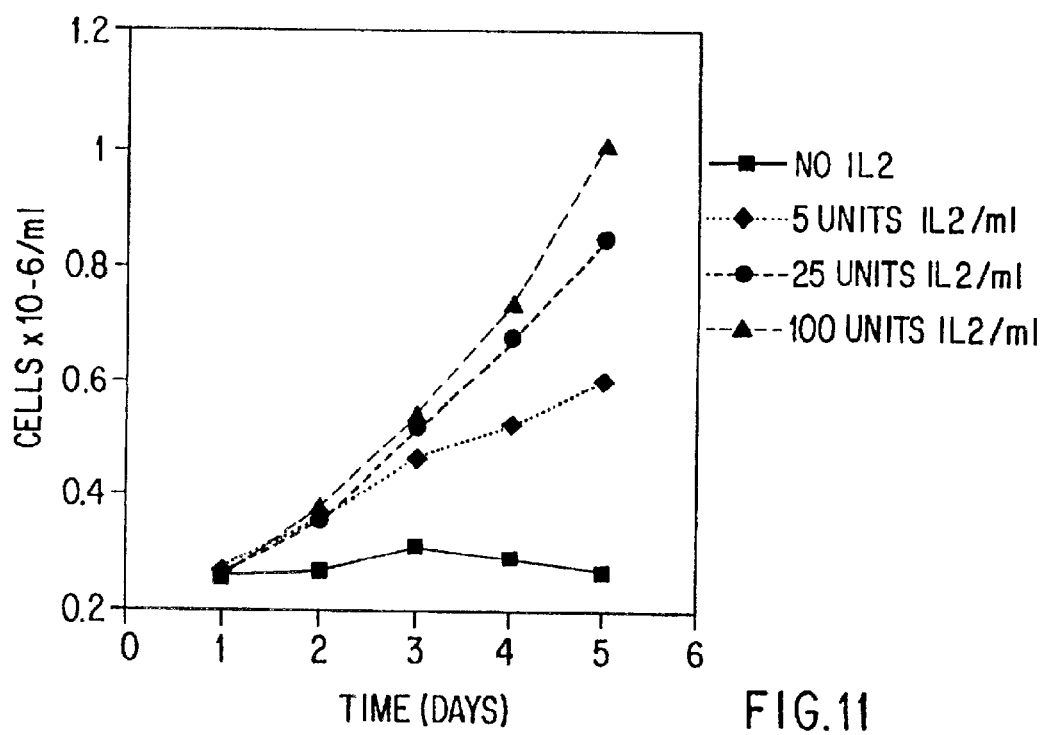

FIG. 11. IL-2-dependence of the HVS-transformed CD8+ cells. The cells were cultured in the presence of 0(■), 5(◆), 25(●), and 100(▲) units of recombinant IL2/ml of AIM-V medium unsupplemented with fetal bovine serum (FBS). Viable cell numbers were ascertained at daily intervals.

Figure 12:
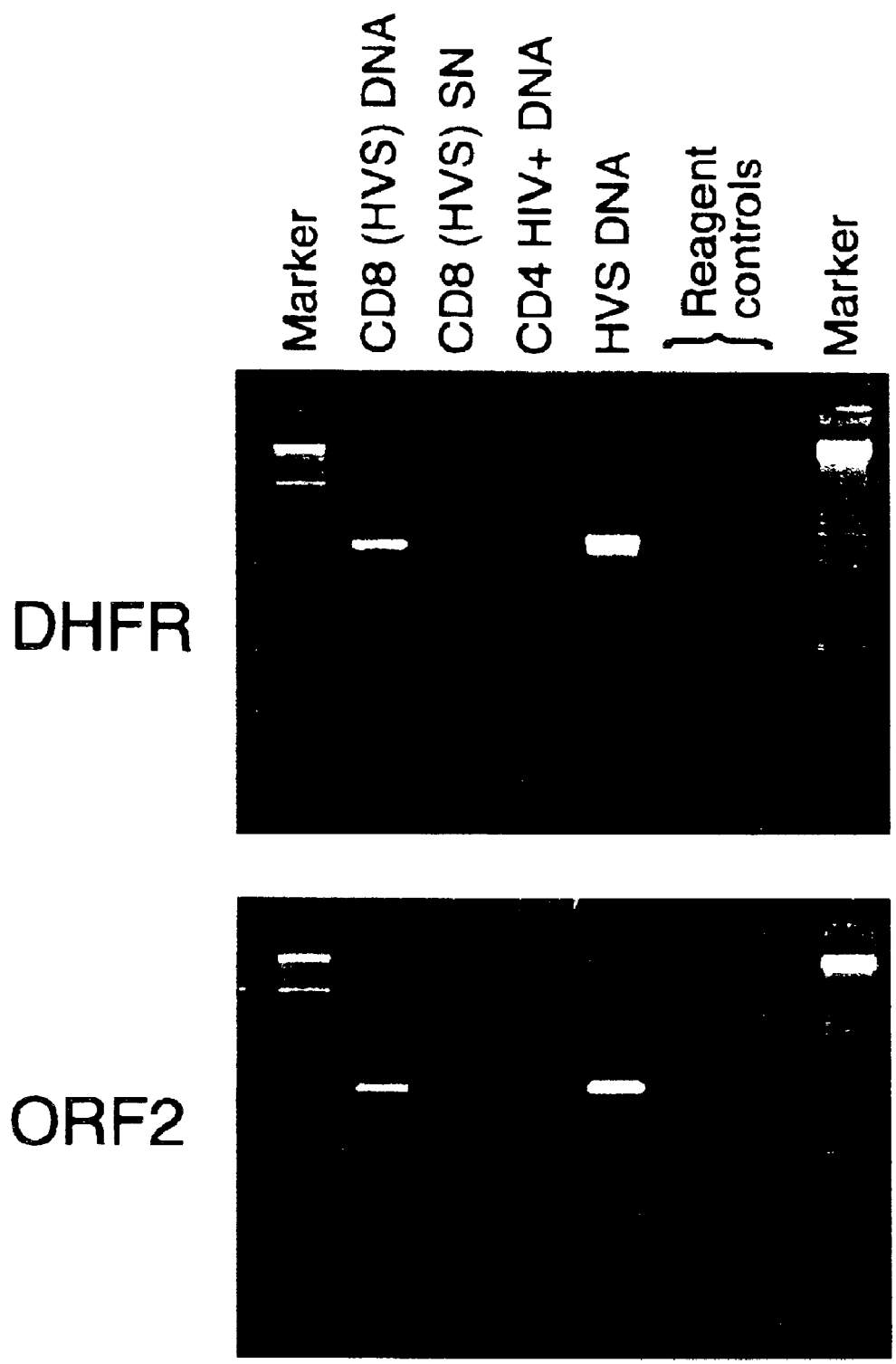

FIG. 12. Detection of HVS DNA sequences in the transformed bulk CD8+ population using the polymerase chain reaction. In the upper panel primers corresponding to the HVS dihydrofolate reductase genes were used. In the lower panel the primers were specific for the HVS ORF 2.

Figure 13:
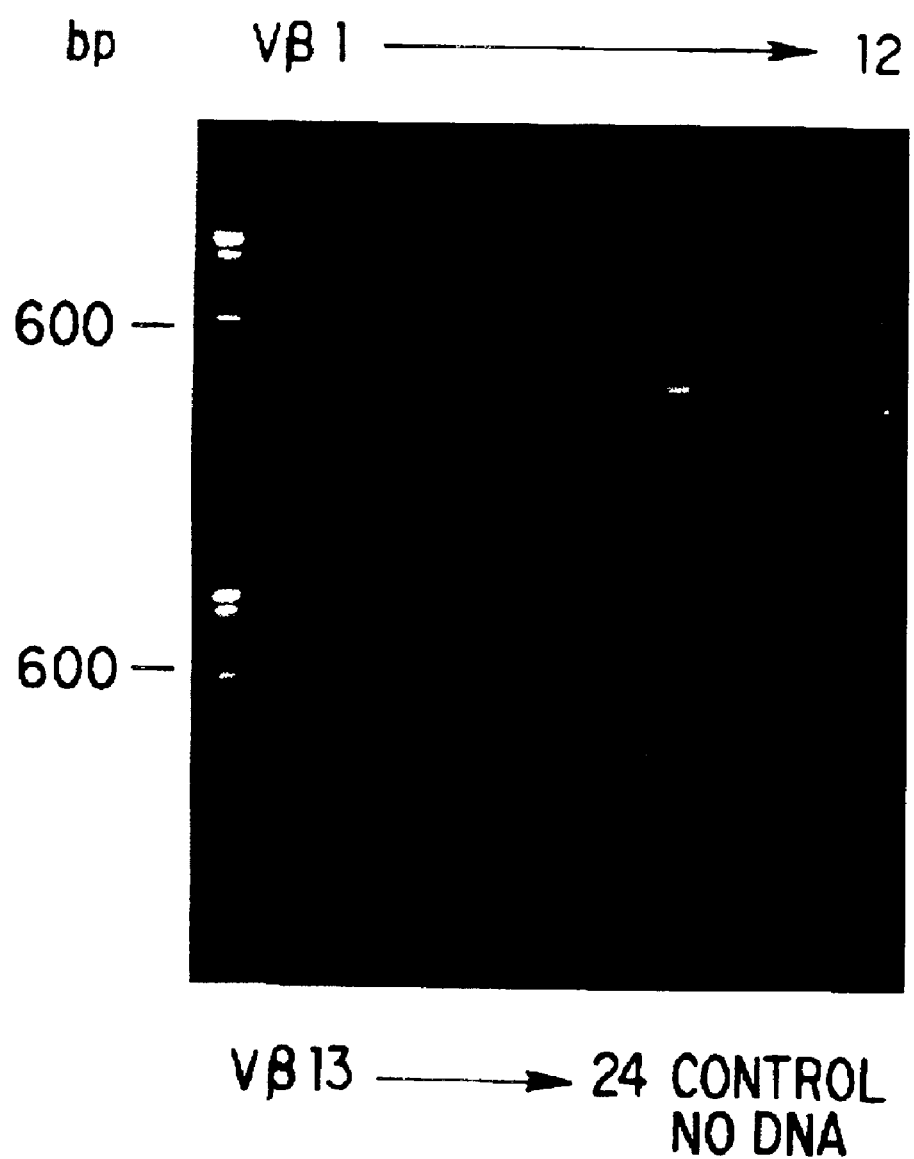

FIG. 13. PCR amplification of the Vβ region of the T-cell receptor genes in the bulk HVS-transformed CD8+ cells from a patient.

Figure 14A:
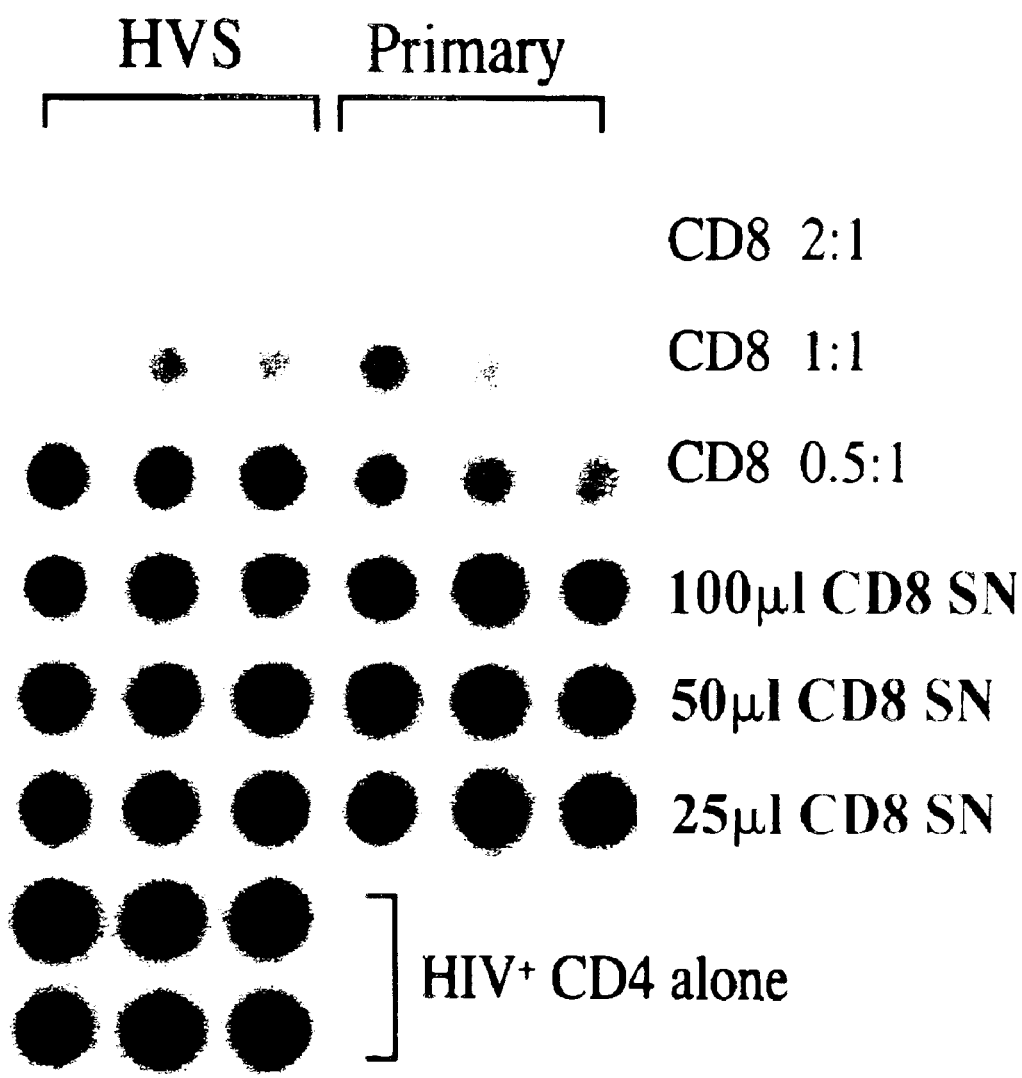
Figure 14B:
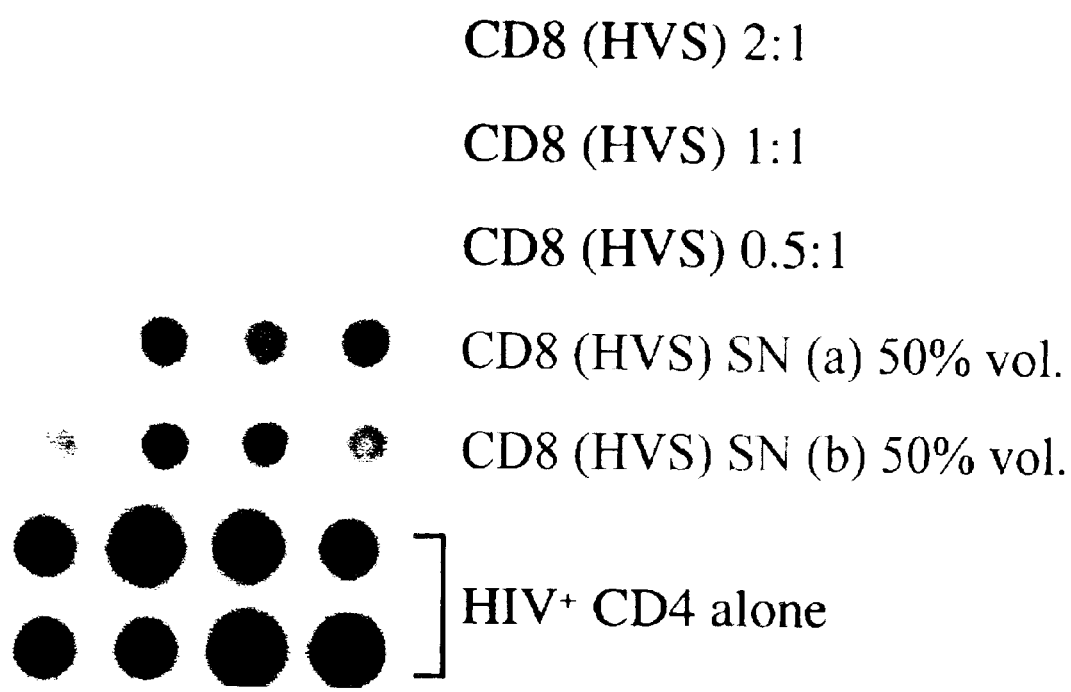

FIG. 14. (A) Comparison of the ability of primary and HVS-transformed CD8+ cells to suppress HIV-1 production by CD4+ cells from the same patient. The figures represent autoradiographs of DE81 membrane-bound RT assay products corresponding to cell culture supernatants. (B) HVS-transformed CD8+ cells can suppress HIV-1 production by CD4+ cells from a MHC class I (MHC-I) mismatched patient.

Figure 15A:
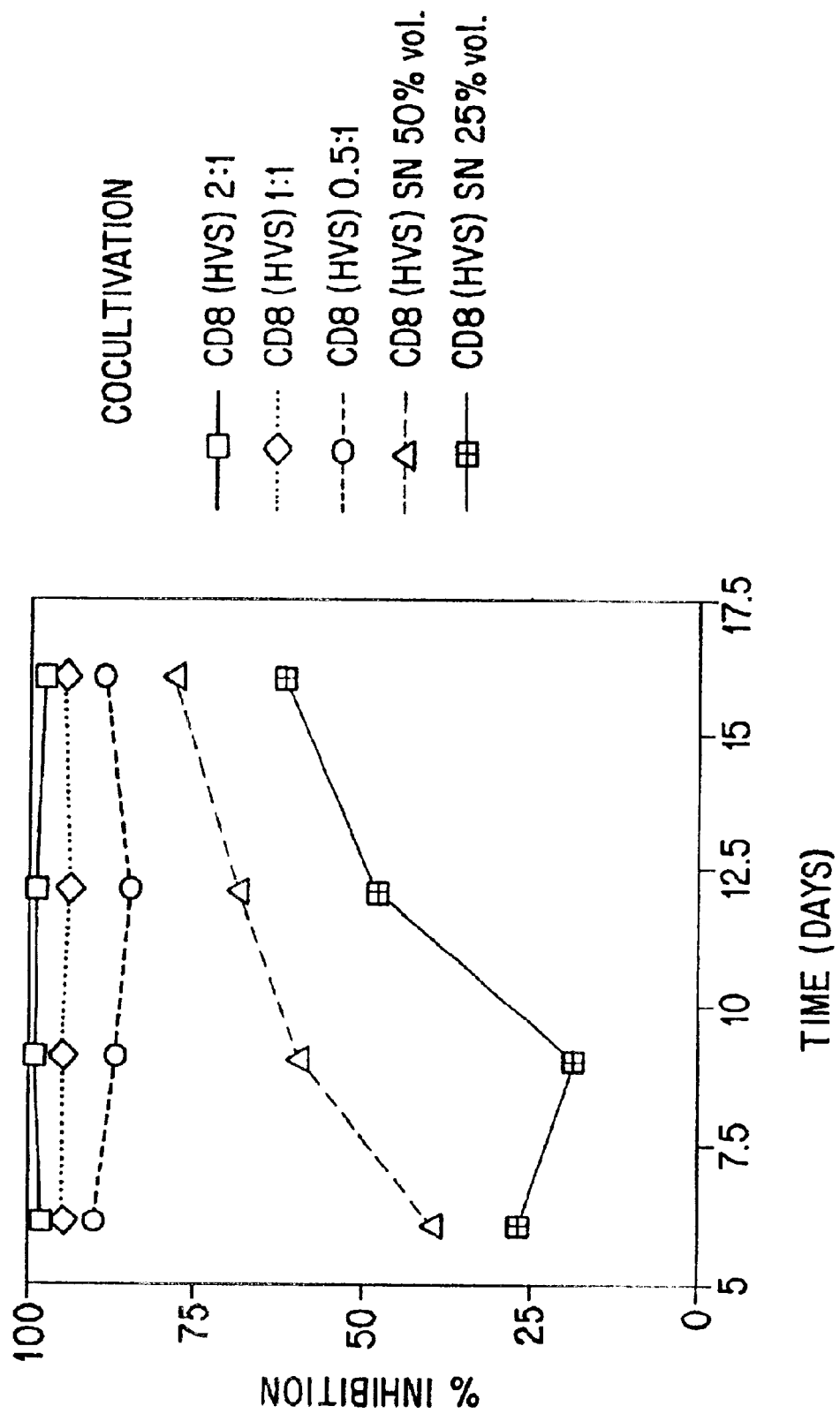
Figure 15B:
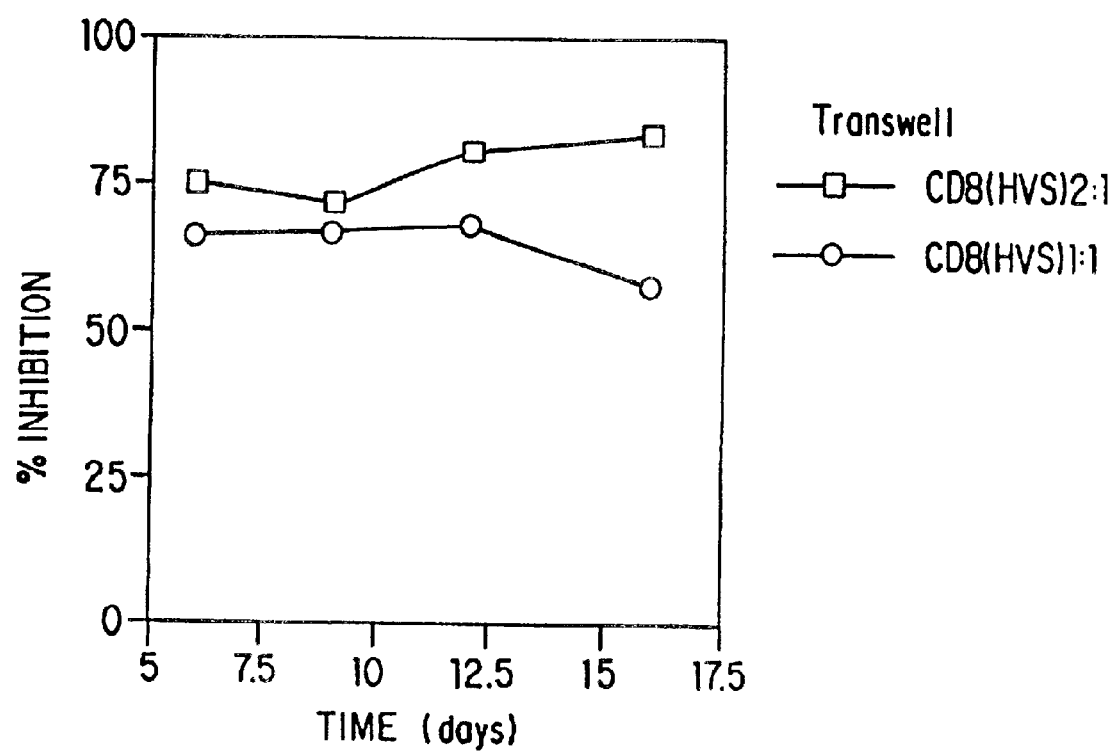

FIG. 15. Comparison of HVS-transformed CD8+ cell inhibition of virus production in transwell and cocultivation assays. (A) A CD4+-CD8+ cocultivation assay was performed in parallel using the same preparations of cells utilized for the transwell study. (B) Transwell experiment using HIV+ CD4+ cells in the upper compartment and HVS-transformed CD8+ cells in the lower compartment at varying ratios to the CD4+ cells. The cultures were sampled at intervals between days 6 and 17. Each point in the cocultivation assay is the average of 3 replicate culture wells.

Figure 16:
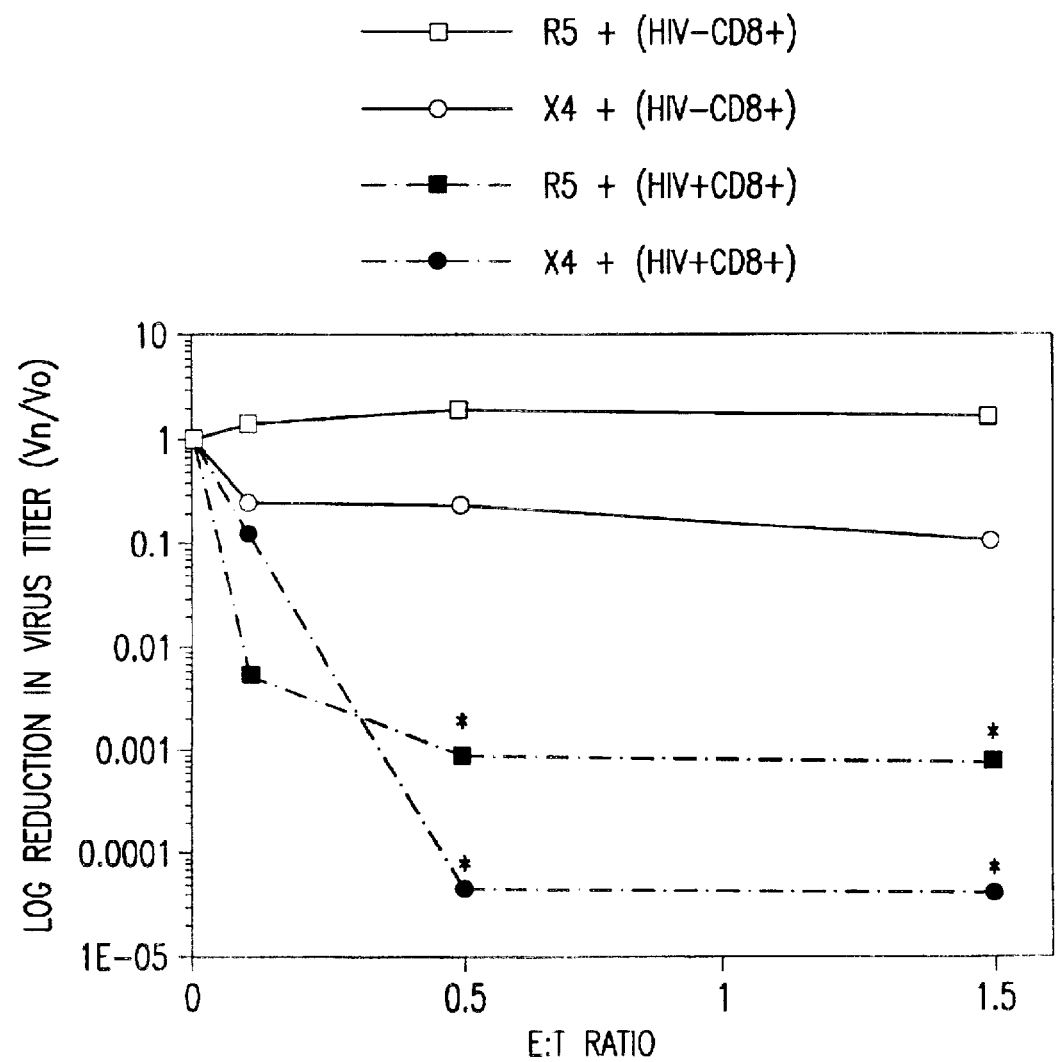

FIG. 16. Data from a quantitative CD8+ suppression assay performed with both a CCR5-dependent or "R5" HIV isolate (QZ4734) and a CXCR4 dependent or "X4" HIV isolate (IIIB) in a 96 well tissue culture plate format using CD4+ enriched cells as the target.

Figure 17:
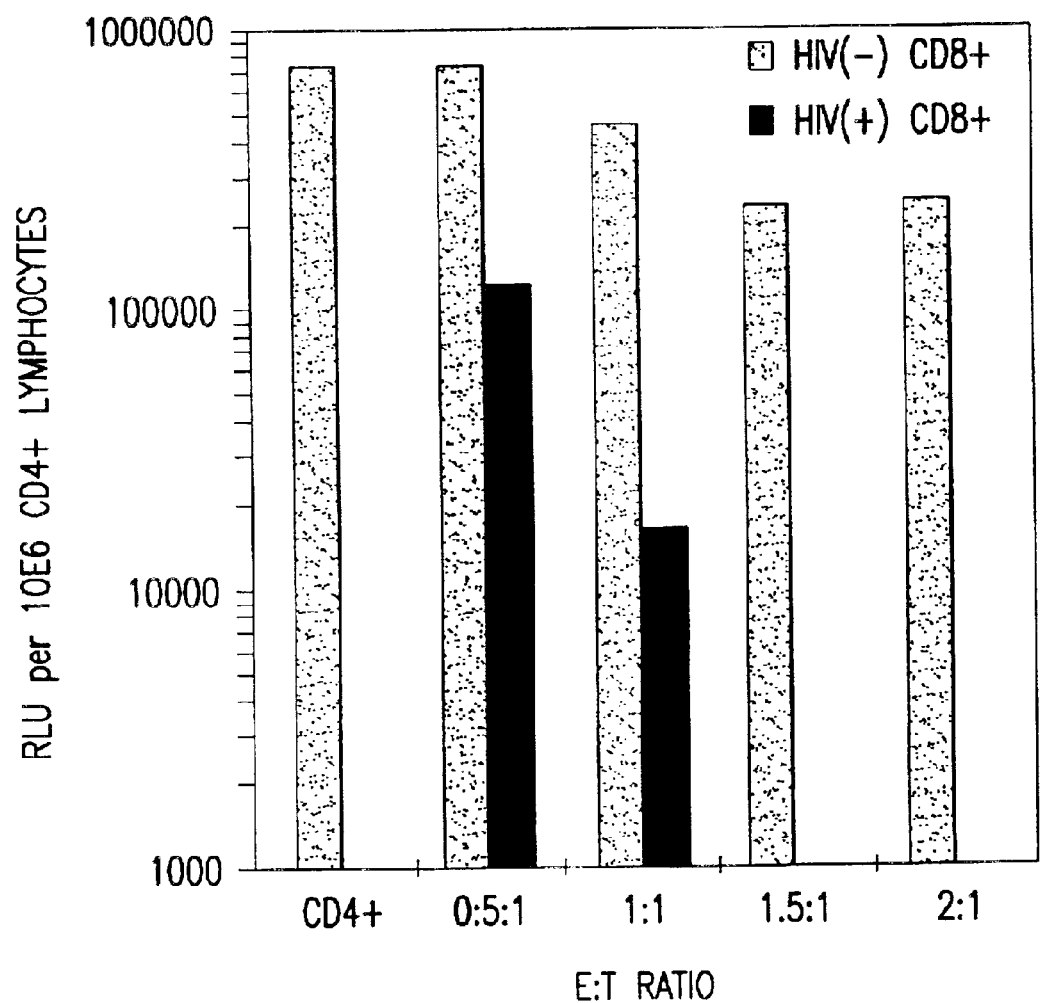

FIG. 17. HIV suppressor activity seen in CD4+ T-lymphocyte cells infectected with a CXCR-4 dependent pseudotyped virus (NL4-3) without CD8+ cells or with CD8+ T-lymphocyte cells from both HIV-positive and HIV-negative individuals; cells were combined at various ratios of CD8+ cells to CD4+ cells (i.e., at various "effector:target" or "E:T" ratios).

FIG. 18. Data from time of addition experiments detecting HIV suppression in CD4+ T-lymphocytes infected with a CXCR-4 dependent pseudotyped virus (NL4-3); (A) CD8+ T-lymphocytes derived from asymptomatic HIV-positive individuals were added to the CD4+ cells at various times after exposure to the pseudotyped virus; (B) the viral entry inhibitors DP178 and anti-CD4+ monoclonal antibody (mAb#19) were added to the CD4+ cells at various times after exposure to the pseudotyped virus.

Figure 19:
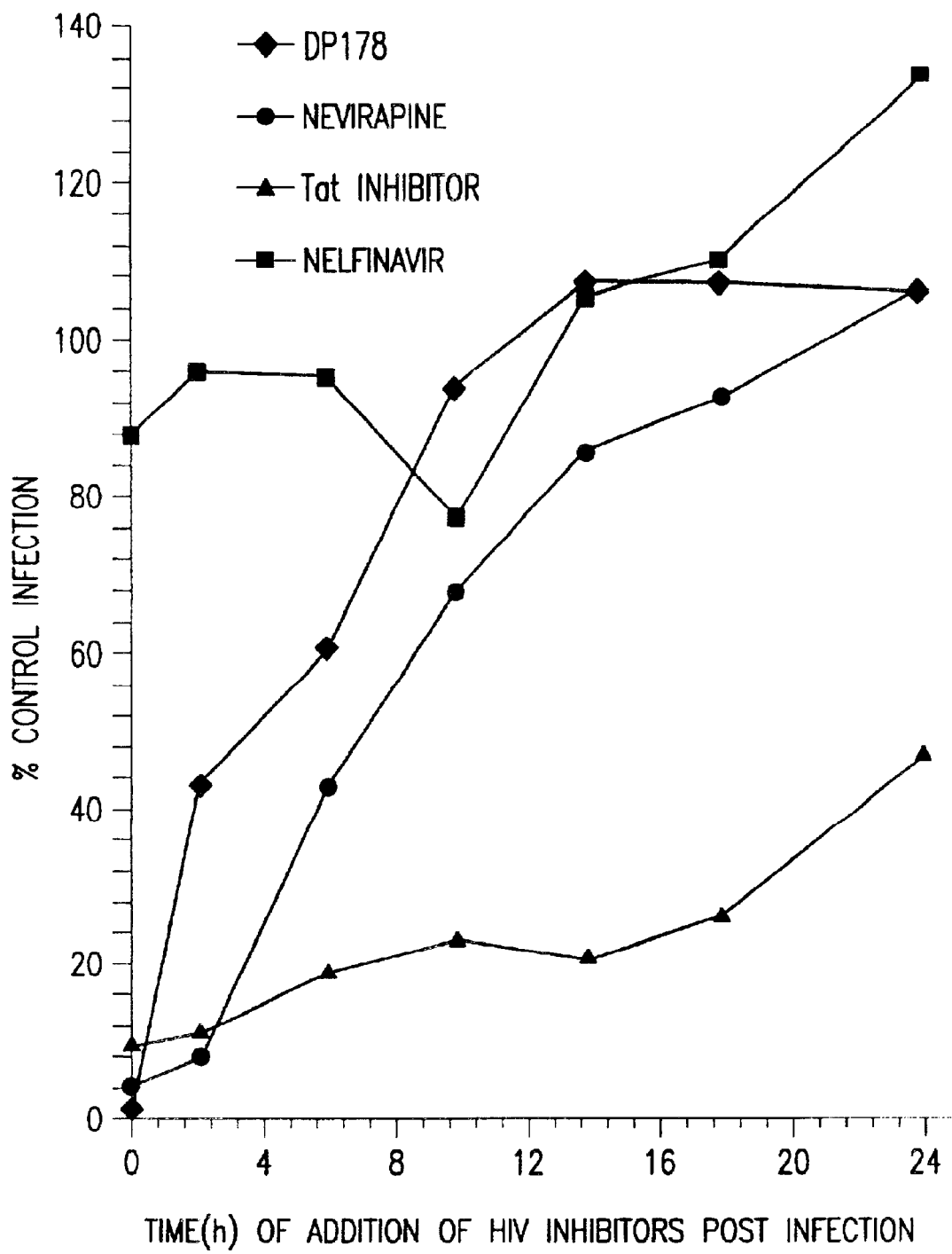

FIG. 19. Data from time of addition experiments detecting HIV suppression in CD4+ T-lymphocytes infected with a CXCR4 dependent pseudotyped virus (NL4-3); the following viral inhibitors were added at various times after exposure to the psuedotype virus: DP178 (20 μg/ml), nevirapine (0.2 μM), nelfinavir (0.2 μM) and Tat inhibitor (50 μM).

5. DETAILED DESCRIPTION OF THE INVENTION

The present invention relates to molecules produced by the CD8+ subclass of T-lymphocytes that are able to inhibit HIV viral replication. The molecules can be e.g., soluble molecules produced and/or secreted by the CD8+ subclass of T-lymphocytes or alternatively, can be expressed on the surface of a CD8+ lymphocyte. The invention further relates to an assay system that can be used for detection of HIV inhibitory activity during a single cycle of HIV infection. In particular, the invention provides a replication deficient HIV pseudotyped virus comprising a reporter vector having a reporter gene that is expressed during early proviral gene expression. In such an assay system, the presence of a suppressor molecule can be detected by measuring the levels of the reporter gene product. As the term is used herein, a "replication deficient HIV pseudotyped virus" refers, specifically, to an HIV pseudotyped virus that is unable to complete a replication cycle. Thus, the replication deficient pseudotyped viruses of the present invention are characterized by their ability to undergo, at most, a single cycle of infection or, alternatively, have the ability to undergo only a portion of a single cycle of HIV infection.

Such an assay system can also be used to identify the stage or stages in the viral replication cycle that are targeted by a suppressor molecule. In a particularly preferred embodiment, the assay system can be used to identify steps up to and including expression of early proviral genes. For example, the Example presented in Section 10, below, demonstrates for the first time, using the assay system of the present invention, that CD8+ suppressor activity targets HIV at a stage of the viral replication cycle after entry of the virus in a cell (e.g., after entry into a CD4+ cell). Thus, the assay system enables a user to both detect a suppressor molecule and characterize its activity.

The invention also provides an assay system for detection of the antiviral activity wherein a reporter gene is cloned adjacent to the HIV viral LTR sequences. The development of the assay system is based on the observation that the suppressor molecule inhibits transcription of genes linked to the HIV LTR promoter sequences. In addition, the invention is directed to the isolation of clonal CD8+ cells that exhibit the antiviral activity (i.e., CD8+ cells that express an HIV suppressor molecule). The invention is further related to the generation of permanently established CD8+ cell lines that express the antiviral activity. Such established cell lines are characterized by their ability to proliferate continuously in tissue culture. Such cell lines may be advantageously used for purification and characterization of the suppressor molecule and/or for cloning of the CD8+ suppressor molecule. The CD8+ suppressor molecule may be used therapeutically to inhibit HIV-replication.

5.1. The CD8+ Suppressor Molecule Inhibits HIV-1 Viral Transcription

The effect of CD8+ cells on HIV-1 replication was investigated by performing experiments in which CD8+ cells, prepared from HIV-1 infected individuals by immunoaffinity techniques, were mixed with virally infected CD4+ cells in a 2:1 ratio. The inhibition of HIV-1 viral replication can be measured by determining the levels of viral reverse transcriptase activity produced by HIV-1 infected cells. As illustrated in FIG. 1, inhibition of viral replication was virtually complete in the presence of CD8+ cells.

Experiments, described in the Example presented in Section 6, below, and in U.S. Pat. Nos. 5,627,023 and 5,861,490 filed on Mar. 29, 1993 and Jun. 6, 1995, respectively, were performed to test whether the mechanism by which the CD8+ suppressor molecule inhibits viral replication is through inhibition of viral gene transcription. A recombinant expression vector was constructed comprising the HIV-1 LTR promoter sequences cloned adjacent to the CAT reporter gene (FIG. 2). The construct was co-transfected into affinity purified CD4+ cells with a second construct expressing the product of the viral Tat gene which is required for viral transcription. A construct consisting of the CAT gene cloned adjacent to the cytomegalovirus immediate early promoter (CMV-IE, FIG. 2) was used as a control (FIG. 2). As indicated in FIG. 3, decreased levels of CAT activity were observed in the presence of autologous CD8+ cells, indicating inhibition of HIV-1 LTR and Tat-mediated HIV-1 LTR transcription in the autologous CD4+ infected cells. Similar experiments were carried out using heterologous CD8+ cells. When these cells were mixed with the transfected CD4+ cells a decrease in CAT activity was also observed (FIG. 4) indicating that compatibility at the major histocompatibility locus (MHC) is not required for HIV-1 suppressor activity. In addition, supernatants derived from CD8+ cell culture exhibited inhibitory activity indicating that at least a portion of the antiviral activity is a soluble factor secreted by the CD8+ cells (FIG. 5).

Additional experiments, which are described for the first time in the example presented in Section 10, below, were performed to more precisely identify the stage or stages of the viral replication cycle which are targeted by CD8+ suppressor activity. The experiments utilize an assay that detects HIV inhibitory activity during a single cycle of HIV infection. The experiments were done using a replication deficient HIV pseudotyped virus comprising a reporter vector having a reporter gene that is operatively associated with the HIV-1 promoter and is expressed in place of an early proviral gene. Such an early proviral gene may be, for example, the HIV nef tat, or rev gene, to name a few. In a particularly preferred embodiment, which was used in the experiments described in Section 10, below, the early proviral gene is the HIV nef gene. Although not limiting of the present invention in any way, the particular, preferred reporter vector used in the experiments described below in Section 10 comprises the reporter virus DNA pNL4-3 LUCR⁻ E⁻—an Env deficient construct containing a luciferase reporter gene in the place of the viral nef gene. Such constructs are known in the art and have been described, e.g., in Connor et al., 1995, *Virology* 206:935–944 and in Chen et al., 1994, *J. Virol.* 68:654–660. The construct was co-transfected into human embryonic kidney cells with a second construct pNL4-3 env, which expresses the product of the viral Env gene. A second pseudotyped virus comprising the reporter virus DNA co-transfected with an expression vector for the amphotropic murine leukemia virus envelope, A-MLV (S-A-MLV-env) was used in an assay to demonstrate that the observed HIV suppressor activity is unrelated to the pseudotyped virus's envelope protein. Thus, the pseudotyped viruses of the invention are not limited to pseudotyped viruses having an HIV Env coat protein, but also include pseudotyped viruses having other, non HIV, protein coats. Such pseudotyped viruses can be readily produced by co-transfecting DNA for such a pseudotyped virus with a vector that encodes for another viral coat protein. For example, a pseudotyped virus used in the methods of the present invention can have a viral protein coat corresponding to the protein coat of murine leukemia virus, vesicular stomatitis virus G (VSV-G) or ebola virus glycoprotein (Ebo-GP), to name a few. Likewise, the pseudotyped viruses used in the methods of the present invention can have a viral coat protein corresponding to the protein coat of any strain of HIV. For example, a pseudotyped virus of the invention can have an Env coat protein of an X4 HIV-1 virus (i.e., an HIV strain that infects T-cells using the CXCR4 receptor). Alternatively, a pseudotyped virus of the invention can have an Env coat protein of an R5 HIV-1 virus (i.e., an HIV strain that infects T-cells using the CCR5 receptor).

The resulting pseudotyped viruses are capable of infecting (i.e., entering) appropriate host cell and undergo reverse transcription, translocation to the nucleus, integration and expression of early virus genes, including Tat, which then acts to upregulate expression of the luciferase reporter. For example, in preferred embodiments wherein the virus has been pseudotyped with an HIV-1 Env protein, the pseudotyped virus is capable of infecting affinity purified CD4+ cells. Thus, the system recapitulates the viral replication process up to and including expression of early virus genes.

Figure 18A:
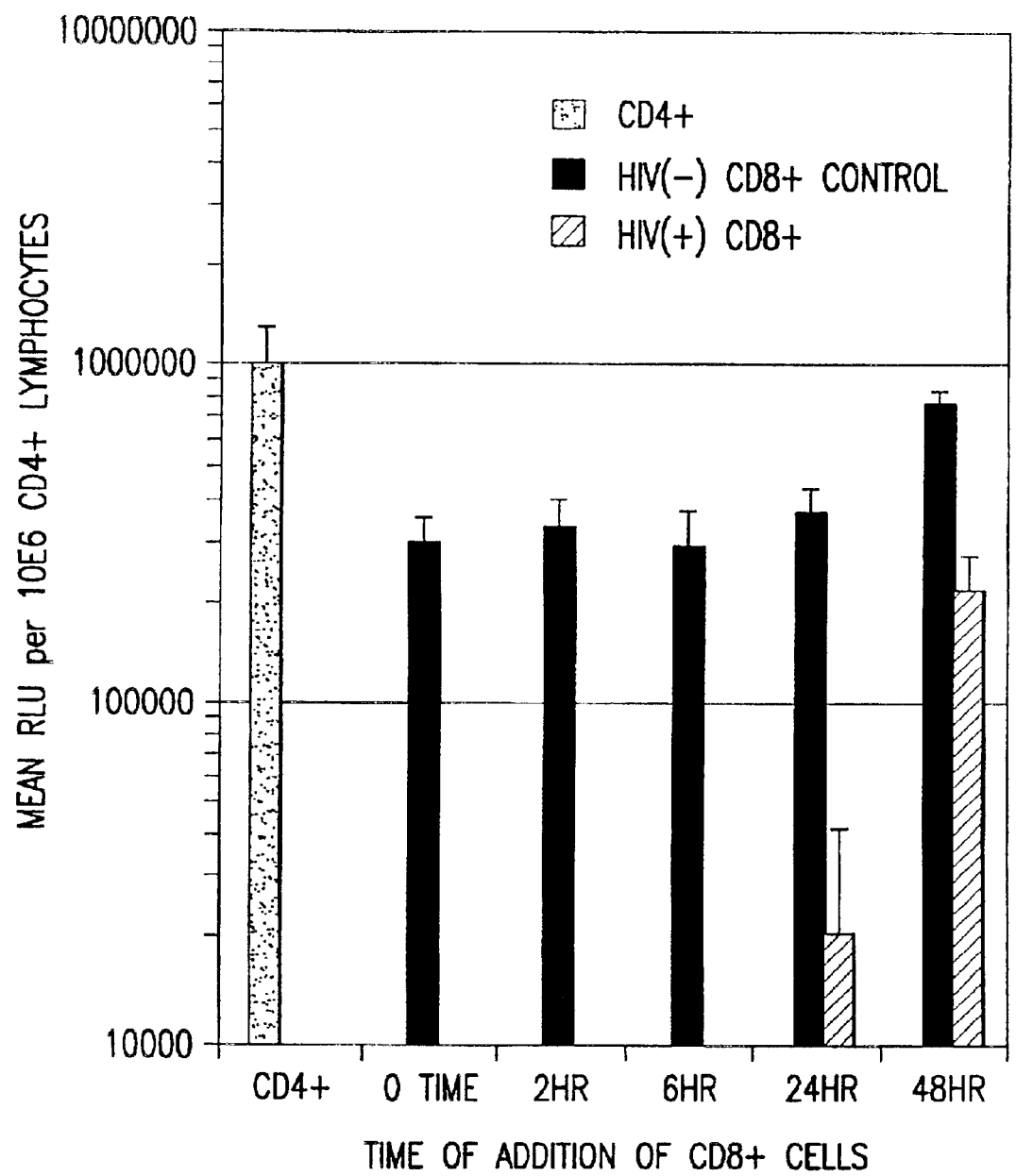
Figure 18B:
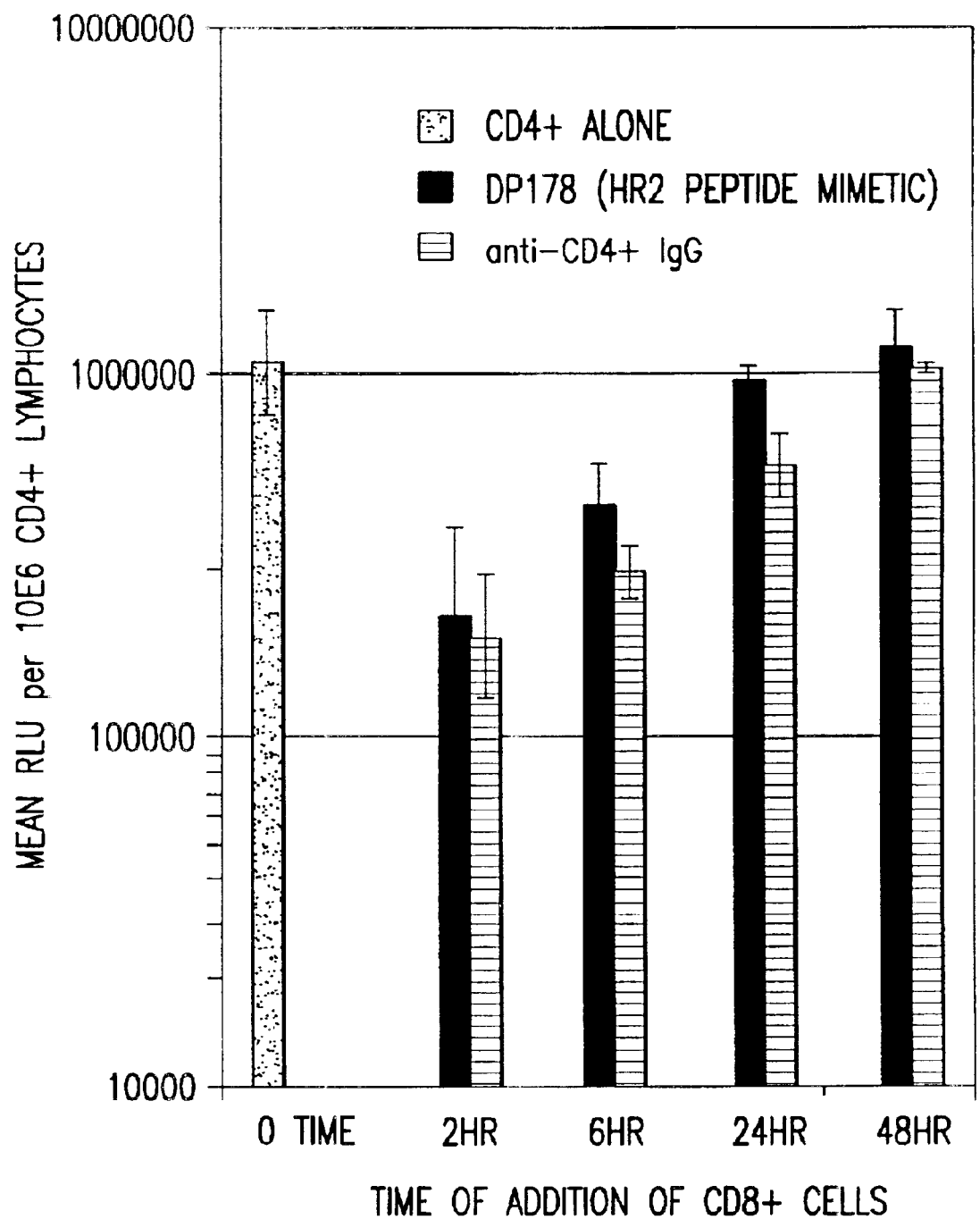

As indicated in FIG. 17, decreased levels of luciferase activity were observed in the presence of CD8+ cells, indicating inhibition of HIV-1 replication before or during the stage of early virus gene expression in infected CD4+ cells. Similar experiments were conducted using CD8+ cells added to CD4+ cells at various times after exposure to the provirus (FIG. 18A) indicating that CD8+ suppression of HIV replication occurs as late as 24 hours post viral exposure. By comparing data from similar experiments using other HIV inhibitors, the stage or stages of the virus replication cycle that are inhibited by CD8+ suppressor molecules could be more precisely identified. For example, time of addition assays with viral entry inhibitors (DP178 and anti-CD4+ mAb) indicate that these inhibitors suppress pseudotyped virus replication within 2–6 hours post virus exposure (FIGS. 18B and 19). By contrast, a reverse transcription inhibitor (nevirapine) suppresses replication within approximately 10 hours post exposure and an inhibitor of early virus gene expression (Tat inhibitor) suppresses pseudotyped virus replication if added as late as 24 hours post exposure (FIG. 19). A protease inhibitor, however, targets a stage of the virus replication cycle after early virus gene expression and does not, therefore, inhibit pseudotyped virus expression in these assays (FIG. 19).

These data demonstrate, therefore, that a target inhibited by a CD8+ suppressor molecule is one which is active during the latest stages of the pseudotyped virus's life cycle. Such targets including, but are not limited to, integration of viral DNA, transactivation from the proviral state, export of Tat and Rev into the cytoplasm and then back into the nucleus and/or Tat mediated enhancement of transcription. In particular, the data presented herein below demonstrates that such CD8+ suppressor activity is not mediated by a compound, such as a beta-chemokine, which inhibits viral entry.

In addition, other viruses of human and animal origin contain similar and/or identical promoter elements as those found in HIV, raising the possibility that the CD8+ suppressor molecule may be of value in the treatment of other viral infections such as HIV-2, HTLV-1 and 2, FeLV, etc.

5.2. Subsets of CD8+ Cells Express Anti-Viral Activity

The availability of CD8+ cell clones expressing antiviral activity will permit extensive surface marker phenotyping of the cells producing this activity. Once the distinguishing phenotype(s) of these cells is established, improved immunoaffinity techniques for purifying these cells can be devised. If these cells play a role in maintaining the asymptomatic state during HIV infection, these markers may be useful for a) clinical staging of infected individuals, b) monitoring the effect of antiviral therapy on disease progression, c) monitoring the effectiveness of therapy with immunological/biological response modifiers, and d) monitoring vaccine response.

Such cell lines may also be used for purification and characterization of the suppressor molecule using methods and techniques described in Section 5.3., infra. The cell lines may also be used as a source of RNA from which cDNA libraries may be constructed as described in Section 5.4., infra.

In a specific embodiment, described herein, CD8+ cells were immunoaffinity purified from the blood of an HIV infected patient and the purified CD8+ cells were subjected to limited dilution cloning. The resulting CD8+ primary cell clones were assessed for their ability to inhibit tat-mediated HIV LTR transcription in autologous B-lymphocytes cell lines transfected with the tat encoding vector and the LTR/CAT expression vector. FIG. 6 shows the level of CAT inhibition observed for three CD8+ primary cell clones. As indicated in the Figure, the clones exhibit varying degrees of inhibition of transcription. Clone 2 (DU. HL-1) shows the greatest inhibition of CAT activity while clone 4 (DU. HL-4) does not inhibit activity.

In alternative preferred embodiments, CD8+ primary clones can be assessed for their ability to inhibit replication of a single cycle reporter vector such as the pseudotyped virus reporter vector described in Section 5.1, above, and used in the experiments presented in Section 10, below. For example, such an assay may be used to screen and identify CD8+ primary clones that suppress pseudotyped virus replication at a particular stage or stages of the virus replication cycle. In one preferred embodiment, such a screening assay can be used to screen for and identify clones that suppress pseudotyped virus replication during the latest stages of pseudotyped virus replication including, but not limited to, during integration of viral DNA, transactivation from the proviral state, export of Tat and/or Rev into the cytoplasm and/or back into the nucleus and/or Tat mediated enhancement of transcription.

As lymphocytes proliferate and differentiate they express cell surface markers which may be used to identify the different classes of lymphocytes present in the body. The different classes of lymphocytes may be sorted based on the differential expression of cell surface markers using antibodies directed to those cell surface markers and flow cytometry. In yet another embodiment of the invention, described herein, flow cytometry was used to measure cell surface markers expressed on the cell surface of clonal populations of CD8+ cells derived from asymptomatic HIV-1 infected patients. The clonal cell lines from each of the individual patients varied in their ability to inhibit HIV replication. As indicated in TABLE I a variety of phenotypic markers are displayed within the suppressive and non-suppressive clonal populations. The suppressive clones tended to express activation markers such as HLA-DR, S6FI, CD25 and CD28 to a much higher degree than non-suppressive clones.

TABLE I

| Phenotypic Marker | Clone | | | | | |
|---|---|---|---|---|---|---|
| | Non-Suppressive | | Suppressive | | | |
| | B5.5 | B18 | B6 | B11 | B22.5 | S92 |
| HLA-DR | 14% | 25% | 13% | 82% | 47% | 72% |
| CD25 | 4% | 17% | 58% | 58% | 16% | 40% |
| CD38 | 4% | 65% | 67% | 90% | 61% | 76% |
| CD28 | 0% | 41% | 64% | 35% | 37% | 16% |
| CD45RA | ND | 5% | 4% | 19% | ND | 34% |
| CD45RO | ND | 45% | 67% | 82% | ND | 65% |
| S6F1 | 23% | 16% | 14% | 59% | 56% | 57% |
| CD57 | ND | 0% | 2% | 0% | ND | 10% |
| TcR (Vβ) | 5.1 | 1 | 5.1 | 12 | ND | 13 |

The increased expression of specific cell surface markers on CD8+ cells expressing antiviral activity will permit the use of improved immunoaffinity techniques for purifying these cells.

5.3. Generation of CD8+ Permanently Established Cell Lines That Express Anti-viral Activity Cultures of normal lymphocytes tend to stop growing after a finite number of generations. Permanent lymphocyte cell lines may be generated by the transfer of genetic information encoding cellular or virally derived oncogenes. The transfer and stable uptake of such oncogenes into the genome of purified lymphocytes will confer on those transformed cells the ability to proliferate continuously in tissue culture.

In an embodiment of the invention permanent CD8+ cells lines were generated by preparing CD8+ cells from HIV+ patients and exposing the purified CD8+ cells to *Herpesvirus saimiri*. One particular transformed culture, acquired from patient 2 and designated DU.WS-1-CD8 (HVS), was chosen for further analysis. As demonstrated in FIG. 12, DU.WS-1-CD8 (HVS) cells contained HSV DNA integrated into their genome as indicated by detection of polymerase chain reaction products of the predicted size. In addition, as presented in FIG. 14 the transformed CD8+ cells were as potent as primary CD8+ cells in their ability to inhibit HIV-1 replication in HIV-infected CD4+ cells. The results presented in FIG. 15 demonstrate that the transformed CD8+ cells produce an inhibitory activity mediated by a soluble factor capable of passing through a membrane.

In an embodiment of the invention permanently established CD8+ transformed cell lines may be generated using a variety of methods. For example, CD8+ cells prepared from HIV+ patients may be transfected with cellular oncogenes such as, for example, ras, src, fos and myc. Alternatively, the CD8+ cells may be transfected with oncogenic viral genes such as EIA of adenovirus, large T of SV40 or middle T of polyoma virus. Additionally, purified CD8+ cells may be infected with various transforming viruses such as Herpes, SV40, HTLV or adenovirus.

Once permanently established cell lines are obtained, they may be subjected to limited dilution cloning. The resulting cell clones may be assessed for their ability to produce the CD8+ suppressor molecule.

The permanently established cell lines of the invention are defined as those CD8+ cells producing antiviral activity and those cells capable of continuous proliferation and propagation in tissue culture. The availability of such transformed cell lines that produce anti-viral activity will facilitate the purification and characterization of CD8+ suppressor molecules.

5.4. Purification and Characterization of CD8$^+$ Suppressor Molecules

A CD8$^+$ suppressor molecule of the present invention is produced by CD8$^+$ cells. In addition, primary cell clones expressing the antiviral activity have been isolated (see Section 5.2., supra). The CD8$^+$ antiviral activity may be isolated, e.g., from the conditioned media of such cells or, alternatively, may be extracted from the cells (for example, in embodiments wherein the CD8$^+$ suppressor molecule is expressed on the cell surface) and subsequently purified to high specific activity. Purification of CD8$^+$ suppressor molecules may be achieved utilizing various procedures and techniques known in the art which include but are not limited to chromatography (e.g., reverse phase liquid, gel permeation, liquid exchange, ion exchange, size exclusion, affinity chromatography), centrifugation, electrophoretic procedures, differential solubility, or by any other standard technique for the purification of proteins.

During any protein purification process, the success of the process depends on the availability of a reliable assay system for measuring the presence of the protein of interest. In an embodiment of the invention, inhibition of HIV-1 LTR and/or Tat dependent HIV transcription may used as an indicator of CD8$^+$ suppressor activity. For example, a recombinant expression vector may be engineered to contain the HIV LTR promoter sequences cloned adjacent to a reporter gene and suppressor activity may be measured by assaying for reporter gene activity. Reporter genes that may be used include, but are not limited to those encoding chloramphenicol acetyltransferase (CAT), firefly luciferase, human growth hormone, or green fluorescent protein. In the assay system described here, the LTR/reporter gene constructs are co-transfected into an appropriate target cell, such as an appropriate primary cell or an appropriate cell line, using transfection methods such as, for example, calcium phosphate transfection, DEAE-dextran transfection, electroporation or liposome-mediated transfection. The transfected cells may then be used to test for the presence of antiviral activity. In a specific embodiment described herein, the HIV-LTR sequences were cloned adjacent to the CAT gene, the construct was transfected into CD4$^+$ cells from HIV infected individuals and the presence of CD8$^+$ antiviral activity was determined by measuring CAT activity (FIG. 3 and FIG. 4).

In another preferred embodiment of the invention, inhibition of a single cycle pseudotyped virus can be used as an assay system to measure the presence of a suppressor molecule of interest. For example, a single cycle pseudotyped virus can be produced which comprises a reporter vector having a reporter gene that is expressed during early proviral gene expression. A pseudotyped virus can be engineered, for instance, to contain a reporter gene in place of an early proviral gene such as the HIV tat, rev or nef gene. In particularly preferred embodiments, the pseudotyped virus contains a reporter gene in place of an HIV nef gene. Reporter genes that may be used include, but are not limited to those encoding chloramphenicol acetyltransferase (CAT), firefly luciferase, human growth hormone, or green fluorescent protein (GFP). For example and not by way of limitation, in the specific embodiment described in Example 10 below, an Env deficient reporter virus construct containing a luciferase reporter gene in the place of the viral nef gene was cotransfected with a second construct which expressed the product of the viral Env gene, thereby producing a pseudotyped virus which is capable of infecting cells expressing CD4$^+$ and an appropriate co-receptor (e.g., CXCR4 or CCR5) and recapitulating viral replication up to the expression of early virus genes.

A known or suspected CD8$^+$ suppressor compound, including a protein of interest in the present invention, can then be screened for suppressor activity by contacting the compound to a cell, e.g., a CD4$^+$ cell, after or concurrently with exposing the cell to the above-described pseudotyped virus and testing for the presence of antiviral activity by detecting expression and/or activity of the reporter gene. The replication deficient HIV pseudotyped virus of the present invention can also be used in screening assays to identify compounds that suppress viral replication at a particular stage or stages of the virus's replication cycle. For example, Section 10, below, describes exemplary "time of addition" assays which determine that a CD8$^+$ suppressor molecule produced by certain cell lines inhibit HIV replication at a stage of the HIV replication cycle after cell fusion and/or viral entry (i.e., after fusion of the cell and viral membranes and entry of the virus into the cell) and during or immediately prior to expression of the early proviral genes.

Time of addition assays of the present invention, including the time of addition assays described, below, in Section 10, simply comprise steps of repeatedly infecting a host cell with a replication deficient HIV pseudotyped virus of the invention followed by contacting the host cell, at different time intervals, with a test compound under conditions such that inhibition of HIV replication can occur and measuring activity of the reporter gene of the replication deficient pseudotyped virus. A host cell can be infected with a replication deficient pseudotyped virus of the invention by simply contacting the pseudotyped virus to the host cell under conditions, which are well known in the art, that permit infection of the host cell by the pseudotyped virus. By observing whether reporter gene activity is increased or decreased after contacting the host cell with a test compound at a certain time interval after viral infection, the skilled artisan can identify the stage or stages during which the test compound inhibits HIV replication. In particular, inhibition of reporter gene activity after a time interval associated with a particular stage in the virus replication cycle indicates that the test compound targets a later stage of the HIV replication cycle.

Time intervals after infection that are associated with particular stages of the HIV replication cycle are already known in the art (see, e.g., Dragic et al., 1996, *Nature* 381:667–673; Srivastava et al., 1991, *J. Virol.* 65:3900–3902). Alternatively, however, a skilled artisan can determine such time intervals without undue experimentation by simply performing the time of addition assays of the present invention using one or more known inhibitors that target and inhibit HIV replication at particular, known stages in the replication cycle. For example, the time of addition assays described in Section 10, below, are also performed using particular inhibitors of cell fusion and viral entry (e.g., DP178 and anti-CD4$^+$ receptor mAb), reverse transcriptase inhibitor (e.g., nevirapine) and an inhibitor of early proviral gene expression (e.g. tat inhibitor) to determine the time intervals associated with each of those stages of HIV replication.

Other compounds that are well known in the art can also be used to identify the time interval after infection during which a particular stage or stages fo the virus replication cycle occur. For example, inhibitors that block viral entry include peptides and peptide mimetics, referred to herein as anti-fusion peptides, which block membrane fusion events necessary for viral entry into a host cell. Many such anti-fusion peptides are well known in the art and include DP178, which is also known in the art as T20 (see, e.g., Bolognesi et al., U.S. Pat. No. 5,464,933 which issued on Nov. 7, 1995), DP107, which is also known in the art as T21 (see, e.g., Wild et al., U.S. Pat. No. 5,656,480 which issued on Aug. 12, 1997), T1249 and T649 (Barney et al. International Patent Publication No. WO 99/59615 which published on Nov. 25, 1999) to name a few. Sequence search motifs are also known in the art and taught, e.g., in International Patent Publication Nos. WO 94/28920 and WO 96/19495, published on Dec. 22, 1994 and Jun. 27, 1996, respectively, by which a skilled artisan can readily identify other anti-fusion peptides that inhibit membrane fusion-associated events such as HIV infection.

Antibodies that inhibit viral entry are also known in the art can be used in time of addition assays of the present invention, e.g., to identify time intervals associated with viral entry. Such antibodies typically bind to a receptor, such as the $CD4^+$ receptor or a co-receptor, e.g., the CCR5 or CXCR4 chemokine receptor, which is involved in or mediates entry of the virus into the host cell. Alternatively, however, monoclonal antibodies that target an HIV protein, preferably a protein such the HIV envlope glycoprotein (gp120), can also be used to inhibit viral entry into a host cell. Many such antibodies are already well known in the art, including anti-$CD4^+$ monoclonal antibody #19 (Endres et al., 1996, *Cell* 87:745–756). Techniques are also well known to produce antibodies, including polyclonal and monoclonal antibodies which target particular proteins such as the cell surface receptor and HIV envlope glycoproteins described above (see, e.g., Harlow and Lane, 1988, *Antibodies: A Laboratory Manual*, Cold Spring Harbor, N.Y.). Other compounds such as CXCR4 attachment inhibitors, including bicyclams such as AMD3100, SID 791, JM3100 and JM2763 (see, e.g., Donzella et al., 1998, *Nat. Med.* 4:72–77), can also be used in time of addition assays of the invention to inhibit cell entry of HIV virus and thereby identify time intervals associated with that stage of the virus replication cycle. Natural ligands for chemokine receptors can also be used in time of addition assay to inhibit cell entry of HIV virus. For example, the CXC stromal cell-derived factor 1 (SDF-1) is a ligand for CXCR4 and can inhibit X4 strains of HIV (see, e.g., Oberlin et al., 1996, *Nature* 382:833–835; Bleul et al., 1996, *Nature* 382:829–832; Lacey et al., 1997, *Proc. Natl. Acad. Sci. U.S.A.* 94:9842–9847). Alternatively, the chemokines RANTES, MIP-1α and MIP-β are CCR5 ligands which can inhibit R5 strains of HIV (see, e.g., Cocchi et al., 1995, *Science* 279:1811–1815; Alkhatib et al., 1996, *Science* 272:1955–1958; Deng et al., 1996, *Nature* 381:661–666; and Dragic et al., 1996, *Nature* 381:667–673). Any of these compounds can be used in the time of addition assays of the present invention.

Time intervals after viral infection that are associated with reverse transcription of the viral RNA genome can also be identified, e.g., by time of addition studies using compounds such as reverse transcriptase inhibitors that block this stage of the viral replication cycle. Reverse transcriptase inhibitors are well known in the art and include both nucleoside and non-nucleoside reverse-transcriptase analogs. Non-nucleoside analogs are preferred in the time of addition assays of the present invention and include compounds, such as nevirapine, delavirdine and efavirenz, to name a few. However, nucleoside derivatives, although less preferable, can also be used, including compounds such as 3'azido-3'thymidine (AZT); dideoxyinosine (ddI); 2',3'-dideoxyadenosine (ddA); 2',3'-dideoxyguanosin (ddG); 2',3'-dideoxycytidine (ddC); 2',3'-dideoxythymidine (ddT); 2'3'-dideoxy-dideoxythymidine (d4T); and 2'-deoxy-3'-thiacytosine (3TC or lamivudime). Halogenated nucleoside derivatives may also be used including, for example, 2'3'-dideoxy-2'-fluoronucleosides such as 2',3'-dideoxy-2'-fluroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides including, but not limited to 2'3'-dideoxy-2',3'-didehydro-2'-fluorothymidine (Fd4T), 2'3'-dideoxy-2'-beta-fluoroadenosine (F-ddA), 2',3'-dideoxy-2'-beta-fluoroinosine (F-ddI) and 2',3'-dideoxy-2'-beta-flurocytosine (F-ddC).

Using standard techniques for protein purification and the assay system described above, the $CD8^+$ suppressor protein may be purified to homogeneity. Once purified, the $CD8^+$ protein may be subjected to microsequencing, using techniques routinely used by those skilled in the art to determine the amino acid sequence of a protein see, Current Protocols in Molecular Biology, Ausubel et al., Green Publishing Associates and Wiley Intersciences, N.Y.) If the $CD8^+$ suppressor molecule is blocked at the amino terminus, the protein may be chemically cleaved or partially enzymatically digested to yield peptide fragments that may be purified and sequenced.

The purified $CD8^+$ protein may be used for production of antibodies to epitopes of the $CD8^+$ protein. Such antibodies include but are not limited to polyclonal and monoclonal antibodies. For production of antibodies, various host animals may be immunized by injection with the $CD8^+$ protein including but not limited to rabbits, mice, rats etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to $CD8^+$ suppressor molecule may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used.

Antibody fragments which contain specific binding sites of the $CD8^+$ suppressor molecule may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments.

Alternatively, Fab expression libraries may be constructed (Huse et al., 1989, Science, 246:1275–1281) to allow rapid and easy identification of monoclonal Fab fragments with the desired specificity to the $CD8^+$ suppressor molecule.

5.5. Cloning of CD8+ Suppressor Molecule

The present invention relates to methods for cloning of the CD8+ suppressor molecule. Using methods which are well known to those skilled in the art, recombinant cDNA libraries may be constructed using RNA prepared from cells known to express the CD8+ suppressor molecule. The cDNA libraries may be constructed using a variety of vector systems, including but not limited to, bacteriophage vectors, plasmid vectors or mammalian expression vectors. See, for example, the techniques described in Sambrook et al., 1989, Molecular Cloning: A Laboratory Manual, Cold Spring Harbor Laboratory, N.Y. and Current Protocols in Molecular Biology, Green Publishing Associates and Wiley Intersciences, N.Y.

The recombinant cDNA libraries may be screened using a number of different techniques. For example, a mixture of degenerate oligonucleotide probes may be designed utilizing the information derived from protein sequencing of the CD8+ suppressor protein (see Section 5.3 supra). The oligonucleotides may be labeled and used directly to screen a cDNA library for clones containing inserts with sequence homology to the oligonucleotide sequences. Alternatively, the oligonucleotides may be used as primers in a polymerase chain reaction. The template for the reaction is cDNA obtained by reverse transcription of mRNA prepared from cells known to express the suppressor activity. The amplified DNA fragment may be labeled and used to screen a library for isolation of full length clones. In another example, an expression library may be screened immunologically using polyclonal or monoclonal antibodies directed against the CD8+ suppressor molecule. In yet another embodiment of the invention, a cDNA library may be engineered into a mammalian expression vector and screened by transfection into the appropriate mammalian cell line followed by assaying for anti HIV suppressor activity in the tissue culture supernatant. Alternatively, in embodiments wherein the HIV suppressor molecule is or is suspected of being a non-soluble molecule (e.g., embodiments wherein the HIV suppressor molecule is expressed or suspected of being expressed on the cell surface), the transfected cell can be contacted with an appropriate target cell, such as an HIV infected CD4+ cell.

In one preferred embodiment of the invention, a subtracted cDNA library may be constructed using RNA prepared from expressing and non-expressing clonal CD8+ cells. The subtracted library may be screened using the LTR/reporter gene assay system. In another preferred embodiment, the subtracted cDNA library may be screened using a single cycle pseudotyped virus assay system, such as the single cycle pseudotyped virus assay described in Section 5.1 and in Section 10, below.

A subtracted cDNA library contains cDNA clones corresponding to mRNAs present in one cell type ([+] cell type) that are not present in a second cell type ([−] cell type). Construction of this type of library enriches for cDNA clones of interest and is used in the isolation of a cDNA clone corresponding to a particular mRNA where the screening procedure is laborious because a specific DNA sequence or antibody is unavailable.

In an embodiment of the invention a subtractive library may be constructed using mRNA prepared from the expressing [+] and non-expressing [−] clonal CD8+ cell lines (see Section 5.2., supra . The [+] cDNA is prepared from cells expressing the antiviral activity and oligonucleotide linkers are ligated onto the ends of the cDNA fragment resulting in endonuclease recognition sites on each end of the cDNA fragment. The [−] cDNA is prepared with blunt ends and digested with a restriction endonuclease that reduces the [−] cDNA fragments to small blunt ended fragments. The [+] cDNA is then mixed with a 50-fold excess of fragmented [−] cDNA, the DNAs are heated to melt apart the double-stranded DNA, and the single stranded DNA is allowed to reanneal. The only [+] cDNA likely to regenerate double stranded fragments with restriction endonuclease restriction sites at each end are those sequences for which no complementary [−] fragments were present. Annealed fragments are ligated in an expression vector having complementary cohesive ends. The resulting cDNA library may be screened using the LTR/CAT expression system.

In yet another embodiment of the invention a method for separating and cloning differentially expressed mRNAs by means of polymerase chain reaction may be used to clone a cDNA coding for the CD8+ suppressor molecule (Liang et al., 1992, Science 257:967). Such a method may be utilized using RNA prepared from expressing and non-expressing CD8+ cell lines.

In addition, gene expression assays using gene expression arrays or microarrays are now practicable for identifying changes in gene expression patterns between different cells (see, e.g., Schena et al., 1995, *Science* 270:467–470; Lockhart et al., 1996, *Nature Biotechnology* 14:1674–1680; and Blanchard et al., 1996, *Nature Biotechnology* 14:1649). Thus, in another, alternative preferred embodiment of the invention, such gene expression arrays or microarrays can be used to compare mRNA expression patterns in CD8+ cells that exhibit HIV suppression activity (e.g., as determined by one of the assays of the present invention) to mRNA expression patterns in CD8+ cells that do not exhibit HIV suppression activity and therefore do not express an HIV suppressor molecule.

5.6. Uses of CD8+ Suppressor Molecules

Currently approved treatments for HIV infection and acquired immunodeficiency disease are pharmaceuticals such as dideoxynucleosides that target viral reverse transcriptase (i.e. AZT, ddI, ddC). Though some clinical benefit has been demonstrated for these agents, drug resistant viral mutants arise limiting their usefulness. Moreover, these agents are only effective against de novo infection and do not exert an antiviral effect against chronically infected or latently infected cells. More effective treatments for HIV infection and AIDS are greatly needed.

The CD8+ subclass of T-lymphocytes produce one or more molecules that inhibit HIV replication suggesting the potential usefulness of such molecules as a therapeutic for treatment of HIV infection and acquired immunodeficiency disease. Because of the ability of CD8+ suppressor molecules to prevent virus production in cells already infected, they can also be of use prophylactically in settings such as vertical transmission of HIV from mother to infant or in acute exposure to HIV. Because the molecules may play a role in maintaining the asymptomatic state of HIV infected individuals, they can further be of use for clinical staging of disease progression, monitoring the effects of immune or biological response modifier therapy and for assessing effectiveness of certain vaccination protocols.

6. EXAMPLE

CD8+ Suppressor Activity Inhibits HIV-1 Replication

6.1. Materials and Methods

Reverse Transcriptase Assays:

Peripheral blood mononuclear cells (PBMC) were prepared from freshly-drawn, anticoagulated blood by standard Ficoll-Hypaque density separation. CD4+ and CD8+ lymphocytes were purified by attachment to anti-CD4+ and anti-CD8+ microCellector flasks (Applied Immune Sciences) according to the manufacturers recommendations, washed extensively, and cultured for 3 days in medium containing RPMI 1640, 20%, v/v fetal bovine serum (FBS), 50 U/ml recombinant IL-2 (Hoffmann LaRoche, Inc.) 50 µg/ml gentamicin sulfate, and 3 µg/ml phytohemagglutinin (PHA, Sigma, Inc.). Cells were removed from the microCellector flasks, aliquots of the CD4+ and CD8+ cell suspensions were analyzed for relative purity by FACS analysis and cell viability was determined by vital dye exclusion. The remaining cell suspensions were cultured for an additional 24 hr in the same medium as above but lacking PHA. CD4+ cells were adjusted to $2 \times 10^6$ cells/ml and 100 µl aliquots were cultured in duplicate or triplicate wells of 96-well microtitre plate with 100 µl of fresh medium or 100 µl of autologous CD8+ cells (adjusted to $4 \times 10^6$ cells/ml), and cultures were incubated at 37° C. in a humidified $CO_2$ incubator. At 24 hr intervals 100 µl aliquots of cultures supernatants were taken, adjusted to 1% Triton X-100 and assayed for reverse transcriptase (RT) activity as described below or frozen at −70° C. until assayed. The cultures were fed with 100 µl of fresh medium each time supernatants were harvested. RT activity was assayed by a modification of the published methods of Goff et al., and Willey et al. 10 µl of triton lysate was mixed with 50 µl of a reaction cocktail containing 50 mM Tris-HCl. pH 7.8, 75 mM KCl, 2 mM DTT, 5 mM $MgCl_2$, 5 µg/ml Poly A, 1.5 µl/ml $OligodT_{12-18}$, 0.05% NP-40, and 10 µCi/ml 32P-TTP, and incubated at 37° C. for 90 min. 40–50 µl aliquots of reaction mixtures were spotted onto either DE-81 paper (Whatmann) or onto NA-45 membranes (Schleicher & Schuell) in a minifold sample filtration manifold (Schleicher & Schuell), and the membranes or paper were washed several times with 2×SSC (0.3M NaCl, 0.03M NaCitrate), followed by 2×SSC containing Bromophenol blue to locate spots. Autoradiography was performed, and the membranes or DE-81 paper counted using a Packard Matrix 9600 Direct Beta Counter. Results presented are the means of duplicate or triplicate wells.

HIV-1 LTR CAT Constructs:

The plasmids used in these studies were as follows: 1) pLTR 18, constructed by inserting the XhoI-BamHI LTR-CAT containing fragment of pU3RIII (Rosen C A, Sodroski J G, Haseltine W A., 1985) into pTZ19R (United States Biochemical) at the Hind III site by blunt-end ligation. Expression of the chloramphenicol acetyl transferase (CAT) reporter gene in this vector is under the control of the HIV-1 LTR promoter; 2) pgtat. a tat expression vector under the control of the CMV-IE promoter (Malim M H., Hauber J., Fenrick R., Cullen B R., 1988); 3) pCMVCAT (kindly provided by Dr. B. Cullen, Duke University Medical Center), expression of the CAT reporter gene in this vector is under the control of the same CMV-IE promoter present in the pgtat vector.

Transfections and CAT Assays:

Purified populations of CD4+ and CD8+ lymphocytes were prepared from freshly-drawn anticoagulated blood as described in Section 6.1.1., except that purified CD4+ and CD8+ cells were expanded in culture for 2–5 days prior to setting up the transfection. To assess effects of CD8+ cells on HIV-1 LTR or CMV-IE transcriptional activity, CD4+ lymphocytes ($20 \times 10^6$ cells) were transfected with 10 µg of plasmid (either pLTR 18 or pCMVCAT) by electroporation using a Bio-Rad Gene Pulser. To assess effects on tat-mediated HIV-1 LTR transcription. $20 \times 10^6$ CD4+ lymphocytes were transfected by electroporation with 2 µg pgtat and 10 µg pLTR 18. The protocol used for the transfections was previously described by Cann et al. (1988, *Oncogene* 3:123–128). The settings used for electroporation were 960 µF, 250 V for a single pulse. 4 ml aliquots of CD4+ cells in fresh medium ($1.25 \times 10^6$ cells/ml) from a single transfection were aliquoted into 4 flasks containing either an equal volume of autologous CD4+ cell conditioned medium, an equal volume of autologous CD4+ cell conditioned medium containing $10 \times 10^6$ non-transfected autologous CD4+ cells, an equal volume of autologous CD8+ cell conditioned medium, or an equal volume of autologous CD8+ cell conditioned medium containing $10 \times 10^6$ autologous CD8+ cells. The volume of each flask was adjusted to 10 ml with a combination of fresh medium (RPMI 1640, 10% heat inactivated FBS, 5% IL-2 (Cellular Products, Inc.) and 1% Pen-Strep (Gibco), and either autologous CD4+ or CD8+ cell conditioned medium so that the final concentration of conditioned medium in each flask was 50%. Cultures were incubated for 48 hr at 37° C. in a humidified $CO_2$ incubator. Cultures were harvested, and CAT activity was determined essentially as described by Ballard et al. (1992, *Proc. Natl. Acad. Sci. U.S.A.* 89:1875–1879), except that 1% Triton X-100 was added to the cell disruption buffer which contained 100 mM Tris-HCl, pH 7.8. CAT activity was not affected by the presence of 1% Triton X-100. Data are plotted for CAT activity in cultures containing autologous CD8+ cells compared to the activity measured in cultures derived from the same transfection containing autologous CD4+ cells. Horizontal lines are drawn to indicate the means of each population. To test tat-mediated transcription in heterologous CD4+ cells a flask containing heterologous CD8+ cell conditioned medium and $10 \times 10^6$ heterologous CD8+ cells was substituted in each transfection. Data are plotted for CAT activity in cultures containing autologous or heterologous CD8+ cells compared to the activity measured in cultures derived from the same transfection containing autologous CD4+ cells.

CAT activity was measured in cell lysates from cultures containing autologous CD4+ cells, cultures containing autologous CD8+ cells and cultures containing autologous CD8+ cells. Each data set from an individual subject was derived from a single transfection. CAT activity is expressed as percent conversion, each assay was based on $5 \times 10^6$ transfected CD4+ cells.

6.2. Results

CD8+ cells prepared from HIV-1 infected individuals by immunoaffinity techniques and stimulated with PHA, inhibit HIV-1 replication in autologous, infected CD4+ cells. The potency of the antiviral effect is striking. When CD8+ cells are incubated with CD4+ cells in a 2:1 ratio, inhibition of viral replication is virtually complete as measured by reverse transcriptase (FIG. 1).

To investigate the mechanism of CD8+ antiviral activity the effect of CD8+ cells on HIV-1 transcription was examined. Autologous and heterologous PBMC-derived CD4+ cells were transfected by electroporation with an HIV-1 LTR CAT construct and a construct that expresses the product of the tat gene. CAT activity was measured in the presence of CD8+ cells and as illustrated in FIGS. 3 and 4, CD8+ cells from HIV-1 infected individuals inhibit tat-mediated HIV-1 LTR transcription in autologous and heterologous CD4+ cells. Experiments conducted with supernatants derived from CD8+ cell cultures indicate that a significant fraction of the inhibitory activity can be found in the supernatant indicating that the suppressor activity is secreted by CD8+ cells (FIG. 5).

7. EXAMPLE

Isolation of CD8+ Clonal Cells Expressing the Anti-HIV-1 Suppressor Molecules

7.1. Materials and Methods

Establishment of CD8+ Cell Clones:

Peripheral blood mononuclear cells (PBMC) were prepared from freshly-drawn, anti-coagulated patient blood by standard Ficoll-Hypaque density separation. Twenty million washed PBMC were incubated with anti-CD8+ bound magnetic microspheres (Dynal, Inc.) at a bead:cell ratio 10:1 in RPMI 1640+1% FCS. After 45' incubation at 5° C. (with occasional resuspension), CD8+ cell/microsphere conjugates were captured on a rare earth magnet, washed twice, and recaptured. The conjugates were transferred to a T-25 tissue culture flask containing 10 ml of RPMI 1640, 20% v/v FBS. 50 mg/ml of gentamicin sulfate, 3 mg/ml phytohemagglutinin (PHA: Sigma, Inc.) and 50 U/ml recombinant interleukin 2 (IL-2; Hoffmann LaRoche, Inc.) Conjugates were incubated at 37° C., 5% $CO_2$ for 48 hours, after which the microspheres were removed by magnetic capture. The remaining CD8+ cells in suspension were analyzed for relative purity by FACS analysis and cell viability was determined by vital dye exclusion. Suspensions of $10^2$ viable CD8+ cells were subjected to limited dilution cloning as follows. All wells of a single 96-well round-bottom plate received 10 cells per well, two 96-well plates were seeded at 1 cell/well, and five 96-well plates were seeded at 0.1 cell/well. All wells of all 8 plates subsequently received $2 \times 10^5$ irradiated (6000 R) heterologous PMBC feeders in the presence of 200 ng/ml anti-CD3 monoclonal antibody (12F6) and 100 U/ml of IL-2. Plates were incubated at 37° C., 5% $CO_2$. At 14 d intervals, 100 μL of cell-free supernatant was removed and discarded. Wells were re-fed with 100 μL of fresh media containing 20% FCS, 200 ng/ml 12F6, and 100 U/ml IL-2 containing $10^5$ irradiated (6000 R) heterologous PMBC feeders. Wells exhibiting macroscopic evidence of cellular proliferation were selected for stepwise expansion into 48-well and 24-well plates and eventually T-25 and T-75 flasks. A 14 d re-stimulation cycle was utilized throughout the expansion of the clonal populations of CD8+ cells. Periodic FACS analyses were performed using an extensive marker panel. Twenty-four hours prior to assay, dead feeder cells were removed by Ficoll-Hypaque sedimentation.

Assay of Transcriptional Inhibition Activity in CD8+ Cell Clones:

CD8+ cells clones were assessed for their ability to inhibit tat-mediated HIV-1 LTR transcription in autologous B lymphocyte cell lines (BLCL) transfected with pgtat and pLTR 18 as follows. Autologous B lymphocyte cell lines were prepared as follows. Peripheral blood was obtained from HIV-1 infected individuals and PBMCs were prepared by Ficoll-Hypaque density gradient separation. Seven to ten million cells were placed in a T-25 flask (Coaster) in 4 ml of cell culture medium (CCM: RPMI 1640, 20% v/v FBS, 50 μg/ml gentamicin). One ml of EBV supernatant harvested from a marmoset cell line (B95-8; ATCC) and 10 μg of cyclosporin A were added to the cell suspension. The flasks were incubated undisturbed at 37° C. in a humidified $CO_2$ incubator for 3–6 weeks. Once a stably transformed BLCL was established it was resuspended in CCM at a concentration of $3 \times 10^5$ cells/ml. Routine cell culture maintenance entailed centrifugation and resuspension in new CCM every 2–3 days. In this manner, exponential growth was obtained with cell viability routinely 85–90%. Autologous BLCL were cotransfected with 0.1 μg pgtat/$10^6$ BLCL and 0.5 μg pLTR 18/$10^6$ BLCL as described in the legend to FIG. 2. Transfected BLCL were aliquoted ($1.5 \times 10^6$ cells) into flasks containing either 50% BLCL conditioned medium, $3 \times 10^6$ autologous CD8+ cells with 50% autologous CD8+ cell conditioned medium (experiment 1) or $3 \times 10^6$ heterologous CD8+ cells with 50% heterologous CD8+ cell conditioned medium (experiment 2), or $3 \times 10^6$ autologous CD8+ clone 2 cells with 50% clone 2 cell conditioned medium, or $3 \times 10^6$ autologous CD8+ clone 4 cells with 50% clone 4 cell conditioned medium, or $3 \times 10^6$ autologous CD8+ clone 29 cells with 50% clone 29 cell conditioned medium. The final volume of each culture was adjusted to 10 ml, and cultures were incubated for 48 hr at 37° C. in a humidified $CO_2$ incubator. Cultures were harvested, and CAT activity was assayed as described in the legend to FIG. 2. Data are presented for CAT activity determined in cultures containing CD8+ cells or CD8+ clones compared to cultures only containing transfected BLCL.

7.2. Results

Peripheral blood mononuclear cells (PBMC) were prepared from blood of an HIV-1 infected individual. CD8+ cells were immunoaffinity purified from the patient's blood and the purified cells were subjected to dilution cloning. The resulting cell clones were assessed for their ability to inhibit HIV-1 LTR transcription in autologous B-lymphocyte cell lines transfected with the HIV-1 LTR CAT and tat encoding constructs. As demonstrated in FIG. 5, the cell clones (clone 2, 4 and 29) vary in their ability to inhibit CAT activity. Clone 2 (DU. HL-2) exhibits the greatest inhibitory activity with clone 4 (DU. HL-4) not inhibiting CAT activity to any significant degree.

8. EXAMPLE

Oligo Clonal CD8+ Lymphocytes From Asymptomatic HIV-infected Individuals Inhibit HIV-1 Replication CD8+ lymphocytes from asymptomatic HIV-1 infected patients are potent suppressors of virus production from infected CD4+ cells. In general, studies of HIV-1 suppression have been performed in the context of bulk CD8+ cell cultures. Described below are experiments wherein suppression by clonal populations of CD8+ cell cultures is demonstrated among the virus suppressive clones derived from an individual patient. A marked heterogeneity between the cells was evident suggesting that CD8+ mediated cell virus suppression is oligoclonal in nature.

8.1. Materials and Methods

Lymphocyte Isolation:

HIV-1 infected asymptomatic volunteers with CD4+ counts >400 were enrolled for this study. Venous blood was obtained under informed consent from all volunteers. Peripheral blood mononuclear cells were prepared from freshly drawn, anticoagulated blood via standard Ficoll-Hypaque density separation. CD8+ and CD4+ lymphocytes were subsequently purified by attachment to anti-CD8+ and CD4+ microCellector T-25 flasks (Applied Immune Sciences, Menlo Park, Calif.) according to manufacturer recommendations. The cells were cultured in the capture flasks with RPMI-1640 medium containing 20% (v/v) FBS, recombinant interleukin-2 (IL-2) (100 IU/ml)(Hoffmann La Roche, Inc., Nutley, N.J.), and gentamicin sulfate (50 μg/ml). In addition, mitogenic stimulation was accomplished with either phytohemagglutinin (PHA [2 μg/ml]; Sigma, St. Louis, Mo.) for CD4+ targets or a combination of anti-CD3 (12F6 [100 ng/ml]; anti-CD28 (100 ng/ml; Becton-Dickinson) antibodies which was used for the CD8+ effector populations.

Cells were cultured for three days at 37° in a humidified $CO_2$ incubator. After harvesting, cell viability generally exceeded 95%. Cell purity of cultures prepared in this manner generally ranged from 87% to 95%, as determined by FACS analysis. Bulk populations were harvested, washed and cultured in the same media (lacking PHA or anti-CD3/CD28) for 3–5 days. CD8+ cells were cloned while CD4+ cells were expanded for use as targets in viral inhibition assays.

CD8+ Cell Cloning:

Bulk CD8+ cultures were plated in 96-well plates (Costar, Cambridge Mass.) at a density of 0.5 and 1 cell/well in RPMI-1640 medium containing 20% (v/v) FBS, recombinant interleukin-2 (100 IU/ml), anti-CD3 (100 ng/ml), anti-CD28 (100 ng/ml) and gentamicin sulfate (50 µg/ml). A total of $1\times10^5$ irradiated (6000 R) allogeneic PBMC/well were added as feeders. Wells with cell growth were expanded in 96 or 48-well plates and restimulated every 10–14 days using the same protocol.

Viral Suppression Assay:

Duplicate or triplicate 100 µl aliquots of either heterologous or autologous CD4+ cells ($1\times10^6$ cells ml) were added to wells of a 96 well microtitre plate. For acute infection, CD4+ cells from a seronegative MHC Class I (MHC-I) mismatched donor were inoculated with approximately $1\times10^4$ TCID$_{50}$ of HIV$_{LAI}$ (derived from CEM cells) for 1 hour in a 37° C. humidified incubator prior to addition of effectors. For screening assays, approximately $1-4\times10^5$ CD8+ cells, within 72 hours of polyclonal restimulation, were added to the autologous CD4+ targets. In titration experiments, CD8+ clones at the same restimulation interval as in the screening assays were used as effectors against autologous and heterologous CD4+ targets at the following CD8:CD4 ratios: 2.0, 1.0, 0.50, 0.25, 0.12. Transwell experiments were performed in 12 well transwell plates with a membrane pore size of 0.4 µm (Costar). $4\times10^6$ CD8+ cells per clone were cultured on the bottom well in 2 ml of culture medium. $1\times10^6$ acutely infected, heterologous CD4+ cells were cultured in the top chamber in 1 ml of culture medium.

The CD8+/CD4+ cell cocultures for both autologous and heterologous assays were incubated for two days. Following the initial two day incubation, 100 µl of supernatant from each well was collected and fresh media was added every other day for the duration of the experiment. For transwell assays, 1 ml from the bottom well and 300 µl from the top well were sampled and replaced with fresh medium. Supernatants harvested from coculture and the top well of the transwell were retained, added to a clean 96 well microtitre plate and mixed with 10 µl per well of a 1% Triton X-100 (Boerhinger Mannheim). Plates were frozen at −70° C. until assayed (within two weeks).

Reverse transcriptase activity was assayed according to the published methods of Goff et al., 1981, *J. Virol.* 38:239; and Willey et al., 1988, *J. Virol.* 62:139 as modified by Chen et al., 1993, *AIDS Res. Hum. Retroviruses* 9:1079–1086. Briefly, 10 µl of the Triton lysate was mixed with 50 µl of reaction cocktail consisting of 50 mM Tris-HCL (pH 7.8), 75 mM KCl, 2 mM dithiothreitol (DTT), 5 mM MgCl$_2$, poly (rA), oligo (dT$_{12-18}$) [Pharmacia, (1.5 µl/ml)], 0.05% Nonidet P-40 (NP-40)m abd $^{32}$P-TTP (10 µCi/ml), and incubated at 37° C. for 90 minutes. After incubation, 40 µl aliquots were spotted onto DE-81 paper (Whatman, Clifton, N.J.) in a minifold sample filtrations manifold (Schleicher & Schuell, Keene, N.H.), washed several times with 2×SSC (0.3 M NaCl, 0.03 M sodium citrate), followed by 2×SSC containing bromophenol blue to mark the spots. Radioactivity was quantified with a Packard Matrix (Meriden, Conn.) 9600 direct beta counter. Percent inhibition, calculated as [1-(RT ACTIVITY IN CD8+CD4+COCULTURE)/(RT ACTIVITY IN CD4+CULTURE)]X100, was determined over the ten day coculture period.

Cytoflourimetric Analysis:

To characterize the phenotype of both suppressive and nonsuppressive clones, three color flow cytometric analysis was performed, using different mixtures of monoclonal antibodies. Cytostat MoIgG1-PE/MoIgG2a-FITC, CD450PE/CD 14-FITC, CD8-PE/CD3 FITC (Coulter, Hialeah, Fla.) were used as dual color premixes in combination with Mouse IgG1-PerCP, CD3-PerCP (Becton Dickinson, San Jose, Calif.) respectively, to determine background fluorescence and lymphocyte purity. Additionally, CD45RO-PE, CD45RA-FITC, CD57-PE, CD28-PE, TCRαβ-FITC, CD38-PE, HLA-DR-FITC (Becton Dickenson), IL-2R-PE (CD25), and S6F1-PE (Coulter) were used with CD8-PerCP. From the three color combinations used, percentages for CD8+ cells expressing CD45RO+, CD45RA+, CD25+, TCR αβ+, CD38+, HLA-DR+, CD57+, S6F1+, or CD38+/HLA-DR+ were determined by using the dual positive population from the two color histogram of the appropriate dye combinations.

In preparation for flow cytometric analysis, the clones were washed five days after restimulation and incubated for 48 hours in fresh medium. The cells were then washed in 3 ml of Dulbecco's phosphate-buffered solution (PBS) (GIBCO, Grand Island, N.Y.) and resuspended in RPMI (GIBCO) at a concentration of $10^6$ cells/ml. Next, 100 µl of the sample was incubated with 5 µl of the Coulter antibodies (2.5 µl for S6F1) and 10 µl of the Becton Dickinson antibodies in the appropriate combinations for fifteen minutes at room temperature. The samples were washed with 3 ml of PBS, resuspended in 250 µl of PBS containing 1% paraformaldehyde, and held at 4° C. in the dark until analysis was performed on a Coulter EPICS Profile II.

8.2. Results

Clonal Suppression of RT Production:

The cloning strategy employed for these studies involved initial capture of CD8+ cells from patient PBMC, followed by plating 0.5 or 1 cell per well in 96-well plates. The overall cloning efficiency ranged from 50–60%. Fifty to seventy-five positive growth wells were randomly selected for the screening assays of viral suppression.

Some CD8+ clones derived from three patients exhibited strong antiviral activity against autologous and heterologous CD4+ lymphocytes. FIG. 7 is a composite showing the effects of representative clones from a typical screening assay. Clones varied in their ability to affect HIV replication. For example, some clones in culture with autologous naturally infected CD4+ cells as well as heterologous naturally or acutely infected CD4+ cells, reduced RT production 95–99% (i.e. S8, B11, and R59), while other clones had little or no effect on RT production (i.e. S6A, B18, R62). Clone B6 was intermediate in the screening assay with inhibition of 65%.

Our routine screening assays examine viral suppression at a single time point on either day 4, 6, or 8 of culture. However, the suppressive effect can extend throughout a ten day culture interval. FIG. 8 is a composite of the original radiographic data from the micro RT assays for two representative clones as well as acutely infected CD4+ cells alone over the course of a 10-day cocultivation period. Significant suppression of RT signal by clone B11 is evident throughout the assay period while the nonsuppressive B18 clone is devoid of suppressive activity.

Of the clones routinely selected from screening, approximately 20% were capable of inhibiting RT activity by 75% or greater, whereas only 4% showed greater than 90% RT inhibition. After screening, clones were extensively evaluated for as long as they could be maintained in culture.

Clonal Suppression in Transwell:

Further evidence to support a soluble factor based and non-cytolytic mechanism of HIV suppression by the clones was obtained with transwell culture vessels which separated cell populations by a 0.4 μM pore-size filter. When CD8+ clones were physically separated from infected CD4+ cells, the hierarchy of suppressive ability among the clones was maintained. The addition of the suppressive clone B11 (4× $10^6$ cells) to the bottom well of the culture vessel resulted in significant virus suppression of acutely infected CD4+ cells (1×$10^6$ cells) in the top well (FIG. 9). Conversely, clone B18 showed little inhibition of virus replication in the same experiment (FIG. 9). A coculture experiment was run in parallel with the transwell experiment. A similar pattern of suppression was evident although suppression was consistently more potent in the coculture assays.

Expression of Cell Surface Markers:

To more clearly define the subsets of CD8+ cells which were capable of virus suppression, we used dual-color flow cytometry to measure surface antigens and RT-PCR to determine the TcR-Vβ expression. The FACS analyses and aforementioned cytokine analyses were performed on the clones at equivalent times in their activation cycle. Moreover, the day when these analyses were performed corresponds to the day the functional suppression analysis was begun. Thus, minor differences appearing among individual clones are not due to differences in the post-activation intervals.

A summary of cell surface marker expression on subsets of CD8+ cells is as follows: Almost all of the clones expressed elevated levels (>45%) of CD45RO and CD38 but reduced levels (<35%) of CD57 and CD45RA. Expression of the activation markers (HLA-DR, S6F1, CD25, and CD28) appeared highly variable. Expression of the activation markers HLA-DR and S6F1 was significantly higher in the three most suppressive clones, B11, B22.5 and S92, than in clone B6. CD25 expression was elevated (>40%) in three of the four suppressive clones. Also, CD28 expression was higher in clone B6 (64%) than in B11 (35%), B22.5 (37%), and S92 (16%). Furthermore, B5.5 and B18 expressed reduced (<25%) levels of HLA-DR, S6F1 and CD25. These data indicated that a diversity of phenotypic activation markers are displayed within the suppressive and nonsuppressive clonal populations with suppressive clones tending to express activation markers to a much higher degree than nonsuppressive clones. The phenotypes have remained stable for at least three months in culture.

In addition to activation marker screening, the Vβ region of the TCR was analyzed to check for both clonality and possible TCR repertoire restriction. Indeed, each clone possessed a single Vβ—indicative of a bona fide clone. The variability in Vβ type indicated that there was no clear pattern of Vβ expression among the clones that correlated with suppressive activity. The only Vβ type which was expressed in more than one clone, 5.1, appeared in both a suppressive (B6) and a nonsuppressive (B5.5) clone. It should also be noted that 4 of the typed clones were from the same individual and no Vβ trends were observed. Collectively, these Vβ and phenotypic data indicate that these CD8+ clones with antiviral activity are phenotypically heterogeneous and do not belong to a specific CD8+ cell subset.

9. EXAMPLE

Generation of Transformed CD8+ Suppressor CD8+ Cells 9.1. Materials and Methods

Preparation of CD8+ Cells:

Venous blood was obtained from asymptomatic HIV+ patients who had been infected for >7 years. PBMCs were prepared by standard Ficoll-Hypaque density separation. CD8+ cells were purified by capture on anti-CD8+ micro-Cellector flasks (Applied Immune Sciences) according to the manufacturer's recommendations, and cultured for 3 days in RPMI 1640 medium supplemented with 10% FBS, 20 units/ml recombinant interleukin 2 (rIL2), penicillin and streptomycin, and 1 μg/ml phytohaemagglutinin (PHA) at 37° C. in a humidified incubator.

Transformation of CD8+ Cells With HVS:

Three days after PHA activation 2.5×$10^7$ CD8+ cells from each patient were resuspended at 2×$10^6$/ml in RPMI 1640 medium supplemented with 20% FBS, 20 units/ml recombinant IL2, penicillin and streptomycin. An equal volume of HVS 488-77 stock was added to an M.O.I of 0.5. The cultures were maintained at 37° C. in a gassed $CO_2$ incubator with as little disturbance as possible, refeeding when necessary with fresh medium. After 1 month the viability as measured by erythrosin red dye exclusion had fallen to 30%. At this point viable cells were recovered by Ficoll-Hypaque separation. The removal of dead cells was repeated as necessary over the following 4 weeks, by which time a transformed growth phenotype was evident.

Virus Suppression Assays:

Virus suppression assays were performed essentially as previously described by Chen et al., 1993, *AIDS Res. and Hum. Retrovir.* 9:1079–1086. CD4+ target cells were prepared from asymptomatic HIV+ patients using CD4 micro-Cellector flasks and were further depleted of CD8+ cells by using anti-CD8+ antibody coated magnetic beads (Dynal). These CD4+ cells were cultured at 2×$10^6$/ml in 100 μl aliquots in 96 well plates. CD8+ cells or supernatants from CD8+ cell cultures were added at varying ratios to a final volume of 200 μl. The medium used throughout was AIM-V medium supplemented with 20% FBS, 20 units/ml recombinant IL2, penicillin and streptomycin. The plates were incubated at 37° C. in a gassed, humidified incubator. At each sampling time point 80 μl of SN was removed, adjusted to 1% Triton X100, and assayed for reverse transcriptase activity. The RT assay method has been described previously (Goff et al., 1981, J. Virol. 38:239–248; Willey et al. 1988, J. Virol. 62:139–147, Chen et al. 1993, AIDS Res. and Hum. Retrovir. 9). After sampling, the cultures were refed with fresh medium or with conditioned supernatant mixed with fresh medium so as to maintain the original assay conditions. Some of these assays were performed using the Transwell system (Costar) in which typically the CD8+ effector cells were seeded in 1.5 mls of medium into the bottom compartment of a 24-well culture plate, and the CD4+ target cells were added to the upper compartment in 500 μl. Sampling was performed from the top compartment as described above, but refeeding was additionally done at this time by removing 1 ml of medium from the lower CD8+ compartment, and replacing with 1 ml of fresh medium.

PCR Analysis of HVS Sequences:

Total DNA was extracted from 1×106 HVS-transformed CD8+ cells and from untransformed HIV+ CD4+ cells by standard phenol/chloroform extraction. DNA equivalent to 3×104 cells was used as the target in PCR reactions employing the following oligonucleotide primer pairs; for the HVS dihydrofolate reductase gene, 5' GAGAGCTCAAAATCAT-AACTAGCT 3' (SEQ ID NO:1)(nucleotides 4057–4080 in the HVS genome: Biesinger et al. 1990) and 5' GGT-TCTTTTGCTAAACTGTATTGTTGCTG 3' (SEQ ID NO:2)(4664–4692); meanwhile, for the HVS ORF2 gene, 5' AGTTCCACACAACTAACTACTAGATGAGAT 3' (SEQ ID NO:3)(1061–1089) and 5' ATGGCAAGCGAAC-CGAACCTAAGATATCCA 3' (SEQ ID NQ:4)(1412–1441). The PCR reactions contained 50 mM KCl, 10 mM Tris-HCl pH8.3, 1.5 mM MgCl2, 100 µM of each of dCTP, dGTP, dATP and dTTP, 2.5 ng of each primer, and 2.5 units of Amplitaq DNA polymerase in a total volume of 100 µl. The thermal cycling conditions were 6 minutes at 95° C., 30 seconds at 45° C., and 3 minutes at 72° C. The PCR products were analyzed on agarose gels containing ethidium bromide.

MHC-Restricted Cellular Cytotoxicity:

The presence of CD8$^+$ cytoxic lymphocytes among the immortalized cells was detected by standard $^{51}$-Cr release assay. Autologous Epstein-Barr virus immortalized B lymphocytes (BLCL) were used as target cells after infection with recombinant vaccinia-HIV constructs. Briefly 1×10$^6$ BLCLs were infected (multiplicity of infection=5:1) for 90 minutes at 37° C. with the following recombinant viruses expressing the *E. coli* lac operon, and the Env, Gag, Pol, and Nef antigens of the HTLV-111B isolate, respectively: vSC8 (Chakrabarti et al. 1985, Mol. Cell. Biol. 5:3403–3409), vPE16 (Earl et al. 1990, J. Virol. 64:2448–2451), vDK1, vCF21 (Flexner et al. 1988, Virol. 166:339–349) and vP1218. Cells were radiolabeled with 100–200 nCi of sodium chromate ($^{51}$-Cr; DuPont, Wilmington, Del.) for 16 hours at 37° and 5% CO$_2$. The cells were subsequently washed, counted and plated at a concentration of 5×10$^3$ viable cells/well plate. HVS-immortalized CD8$^+$ lymphocytes were used as effectors at the E:T ratios of 100 and 50:1; each E:T was tested in triplicate. Targets plus medium or 0.5% Triton X-100 were used as control for spontaneous (SR) and maximum release (MR) respectively in 4 hour-assay. The percentage of specific lysis (%SL) was calculated according to the formula [(cpm experimental release) minus (cpm SR)]/[(cpm SR)]×100. Spontaneous release did not exceed 20% MR.

The presence of anti-HIV CTL activity was defined as positive if the % SL against BLCL expressing HIV antigens was 10% higher than the % SL against the control.

Cloning of CD8$^+$ (HVS) Cells:

The bulk transformed CD8$^+$ cells were resuspended in fresh culture medium (AIM-V medium supplemented with 20% FBS, 20 units/ml recombinant IL2, penicillin and streptomycin) in a 15 ml tube and left to stand for 1 hour to allow cell aggregates to sediment. The cell suspension was then counted and diluted before plating in 96-well culture dishes at 0.25 cells per well. 5×10$^3$ irradiated PBMCs were added to each well as feeders. The cultures were fed at weekly intervals with fresh medium and expanded as necessary.

9.2. Results

Establishment of Transformed CD8$^+$ Cell Populations:

CD8$^+$ cells were prepared from several asymptomatic HIV$^+$ patients, activated with PHA for 3 days and then exposed to HVS. After approximately 30 days we observed cessation of cell growth and a rapid decline in cell viability in some of our cultures (patients 1 and 3). In another culture (patient 2) we observed continuous activation-independent growth against a background of cell death, consistent with the expansion of a transformed sub-population (FIG. 10). All the studies described in this work were conducted using later passages of the transformed culture from patient 2. The growth properties of this culture were examined by seeding 5×10$^6$ cells into 10 mls of AIM-V medium (unsupplemented with FCS), containing varying concentrations of rIL2 for approximately 60 hours (FIG. 11). The growth of this population declines if it is moved to serum free medium for extended periods of time (>3 weeks). The experimental results described in the following sections were performed on later passages of the transformed culture from patient 2.

Detection of HVS DNA Sequences in Transformed CD8$^+$ Cells:

Total cell DNA was prepared from the CD8$^+$ (HVS) cells 60 days after exposure to HVS. PCR was performed using primers corresponding to the viral dihydrofolate reductase gene and to ORF-2. The latter, also designated STP-C488, has been reported to have transforming and tumor-inducing activity and to be responsible for the viral transforming phenotype (Jung et al. 1991, Proc. Natl. Acad. Sci. USA 89:7051–7055). We obtained PCR products of the predicted sizes using the DNA from the transformed cells as a target (FIG. 12). When we used an extract prepared from the conditioned medium used to cultivate these transformed cells we saw no HVS PCR signals, indicating that no virus-associated DNA was present in the medium. This correlates with findings that when this cell-free conditioned medium was used to overlay a HVS-susceptible monolayer of OMK cells for extended periods no viral CPE or plaque formation is observed. We obtained an upper limit for infections HVS of less than 0.1 pfu/ml. These observations, taken together, indicate that the transformed cells stably contain HVS DNA sequences, but that no infectious virus is being secreted by these cells.

Transformed CD8$^+$ Cells Are Polyclonal and Activated:

RNA was prepared from the CD8$^+$ (HVS) cells, and cDNA synthesized and analyzed using PCR primers corresponding to the V$_\beta$ region of the T-cell receptor gene. We found that 22 of the 24 V$_\beta$ families were represented in the bulk population (FIG. 13), indicating that our transformed CD8$^+$ culture is polyclonal. We also analyzed the surface marker phenotypes by fluorescence activated cell sorting (FACS) and found that the predominant markers were: CD8, CD25, CD38, S6F1, CD45RO, CD28 and HLA-DR. No CD4$^+$ expression was detectable in the population by FACS analysis. The CD25, CD38 and HLA-DR markers are all typical of activated T-cells, the CD25 molecule being the IL-2 receptor. The presence of this marker on the surface of the majority of the cells may correlate with our observation of an IL2-dependent growth phenotype. The CD45RO surface marker indicates that the population is primarily comprised of memory cells.

Transformed CD8$^+$ Cells Do Not Exhibit CTL Activity:

To ascertain whether the CD8$^+$ (HVS) cells contained a significant CTL subpopulation four hour [$^{51}$Cr] release CTL assays were conducted employing as targets EBV transformed BLCL cells infected with vaccinia constructs expressing the HIV-1 env, gag, pol and nef proteins as targets. Despite using a high ratio of effector to target cells, we observed no significant HLA-restricted cytolysis compared to the vaccinia vector control.

Transformed CD8$^+$ Cells Secrete a Soluble Factor That Inhibits HIV-1 Replication:

To compare the inhibitory activity of the HVS-transformed CD8$^+$ cells with that of primary CD8$^+$ cells from the same patient, autologous suppression assays were set up by isolating CD4$^+$ cells from the patient and then cocultivating them with the CD8$^+$ cells at defined ratios. The culture supernatants were sampled at regular intervals and assayed for reverse transcriptase activity. The results (FIG.

14A) indicated that the transformed CD8+ cells were very similar to the primary CD8+ cells in their ability to inhibit HIV-1 production by the autologous CD4+ cells. To test whether this observed inhibition was MHC-I restricted, a similar assay was performed employing CD4+ cells from a completely MHC-I mismatched HIV-1 patient. Inhibition that was as potent as that seen in the autologous assay (FIG. 14B), was observed. The level of suppression with a CD8+:CD4+ ratio of 2:1 approached 98%. These observations, together with the lack of detectable activity in the CTL assays, indicates that the observed inhibition is not due to MHC-I restricted CTL activity.

A transwell assay system in which the effector cells are separated from the target cells by an 0.4 µm membrane was used to investigate whether the inhibition of virus production by HIV-1 infected CD4+ cells requires cell-to-cell contact. The results from this assay (FIG. 15) indicate that, while the most potent suppression is seen with cocultivation, at least part of the inhibitory activity is mediated by a soluble factor capable of passing through the membrane. In addition, experimental results indicated that the conditioned medium from the transformed CD8+ cells can inhibit virus production by the infected CD4+ cells. The level of inhibition seen is comparable to that in the transwell experiments. Of note is the observation that the degree of inhibition increased during the course of the experiment. This may be due to the fact that the cultures were refed with more conditioned CD8+ supernatant at each time of sampling.

10. EXAMPLE

The CD8+ Suppressor Molecule Inhibits HIV After Viral Entry

Additional studies were conducted to more precisely determine the stage or stages of the HIV replication cycle that is or are susceptible to inhibition by a CD8+ suppressor molecule and/or by CD8+ cells. In particular, the studies described in this section were designed to determine whether a juncture exists after the initiation of virus infection that is resistant to CD8+ suppressive effects.

10.1. Materials and Methods
Preparation and Transformation of CD8+ Cells:

Peripheral blood mononuclear cells (PBMC) were prepared from freshly-drawn, anticoagulated venous blood from asymptomatic HIV-positive individuals by standard Ficoll-Hypaque density separation. Cells were activated for 3 days with anti-CD3 (OKT3) and anti-CD28 antibodies in AIMV medium (Sigma) supplemented with 10% FBS, recombinant interleukin 2 (rIL-2, 20 units per ml), streptomycin (50 µg/ml) and gentamicin (10 µg/ml) at 37° C. in a humidified $CO_2$ incubator. CD4+ cells were removed by positive selection with anti-CD4+ antibody coated beads (Dynal, Lake Success, N.Y.). CD8+ cells were further purified by positive selection with anti-CD8+ antibody coated beads (Dynal, Lake Success, N.Y.). Beads were removed by DetachaBead (Dynal).

The CD8+ cells of two asymptomatic subjects, displaying the most potent activity against an X4 HIV insensitive to β-chemokines in a quantitative assay described hereinbelow were chosen for further characterization. The cells were transformed substantially as described in Section 5.3, above, and by Lacey et al, 1998, *AIDS Res. Hum. Retroviruses* 14:521–531, using the herpesvirus saimiri (HVS) subgroup C strain 48877 to transform the CD8+ cells and create continuous cell lines.

Quantitative CD8+ Suppression Assay:

Peripheral blood mononuclear cells were prepared from freshly drawn HIV-negative pooled donors and separated by standard Ficoll Hypaque density separation. PBMCs were activated for 2–3 days with anti-CD3 antibodies (OKT3) and anti-CD28 antibodies. CD4+ and CD8+ were obtained by negative selection with anti-CD8+and anti-CD4+ coated beads, respectively. CD4+ cells were centrifuged and resuspended in fresh medium at $2.0\times10^5$ cell/ml. Duplicate 100 µl aliquoats were cultured in wells of a 96-well microtiter plate containing 20 µl of serially diluted virus: either QZ4734, a non-syncytia-inducing HIV-1 primary isolate (R5), or IIIB, a syncytia-inducing HIV-1 laboratory strain (X4). Fresh media or CD8+ cells at at various effector to target ratios were added in 80 µl. Cultures were incubated at 37° C. in a humidified $CO_2$ incubator. At 72 hour intervals, 90 µl of supernatant was removed and adjusted to 1% with TritonX-100, and cultures were fed with an equal volume of fresh media. The supernatants were assessed for virus replication by measuring reverse transcriptase activity according to the method of Chen et al., 1993, *AIDS Res. Hum. Retroviruses* 9:1079–1086.

Creation of Pseudotyped Virus, Infection and Luciferase Assays:

Pseudotyped viruses were produced by transfection of DNA into the human embryonic kidney cell line, 293T, using the modified calcium phosphate method described by Connor et al., 1995, *Virology* 206:935–944. The virus containing supernatants were harvested three days later. Both a reporter virus DNA (pNL4-3 LUCR$^-$E$^-$) and an expression vector for an HIV-1 envelope protein, pNL4-3, were cotransfected.

CD4+ primary T-lymphocytes were infected for two hours at 37° C. with 100 µl of pseudotyped virus. The initial cell concentration was $1.8\times10^6$ cells per ml. After 72 hours, cells were washed with phosphate buffered saline and lysed in 1×luciferase lysis buffer (Promega) followed by one freeze-thaw cycle. The sample was assayed with the Promega Luciferase Assay System and a luminometer (Lumat LB 9501, EG&G Berthold). In certain experiments, DP178 (20 µg/ml), anti-CD4+ monoclonal antibody #19 (20 µg/ml), nevirapine (0.2 µM), nelfinavir (0.2 µM) or a tat inhibitor (50 µM) were added either simultaneously with the virus or at timed intervals following infection.

10.2. Results
Establishment of CD8+ Cell Clones Expressing the HIV-1 Suppressor Molecule:

CD8+ T-lymphocytes from ten asymptomatic HIV-positive individuals were screened for inhibition of X4 HIV-1 virus replication. CD8+ T-cells from two subjects exhibiting the most potent activity were subsequently transformed with Herpesvirus saimiri (HVS) to develop cell lines with this effector phenotype according to the methods described by Lacey et al., 1998, *AIDS Res. Hum. Retroviruses* 14:521–531. These cell lines, which are referred to herein as DU.JR-HVS and DU.HS-HVS, were deposited with the American Type Culture Collection (ATCC; Manassas, Va.) on Mar. 14, 2000 as described in Section 11, below, and given the Accession Nos. PTA-1551 and PTA-1552, respectively.

Data from a quantitative CD8+ suppression assay with these cell lines is shown in FIG. 16. The assay characterizes the CD8+ T-cell activity against the X4 IIIB HIV-1 virus and an R5 HIV-1 primary isolated referred to as QZ4734. Non-transformed CD8+ enriched cells from a pool of normal donors did not significantly alter viral titer of either virus. However, the HVS-transformed CD8+ cells from an asymptomatic HIV-positive individual potently inhibited infection of both the QZ4734 and IIIB viruses.

In more detail, when transformed $CD8^+$ cells were incubated with $CD4^+$ cells at a ratio of only 0.1 to 1, the $CD8^+$ cells reduced the R5 HIV viral titer by greater than two logs. Increasing the ratio to 0.5 to 1 completely blocked infection at all virus input levels tested, yielding a lower limit of a three log reduction in R5 HIV-1 titer. Similarly, for X4 HIV-1 virus challenge, incubating $CD8^+$ cells with $CD4^+$ cells at a ratio of 0.5 to 1 blocked replication completely at all levels examined, causing at least a four log reduction in X4 titer.

It is interesting to note that X4 HIV-1 isolates are isolates which infect T-cell lines using the CXCR4 chemokine receptor, whereas R5 HIV-1 isolates infect T-cells using the CCR5 receptor. X4 HIV-1 isolates are typically recovered late in the course of HIV infection and have been shown to be insensitive to β-chemokines (see, e.g., Cocchi et al., 1995, *Science* 270:1811–1815; Dragic et al., 1996, *Nature* 381:667–673; Alkhatib et al., 1996, *Science* 272:1955–1958; Deng et al., 1996, *Nature* 381:661–666; and Cocchi et al, 1996, *Nat. Med.* 2:1244–1247). Thus, the results presented here indicate that a $CD8^+$ suppressor is inhibiting HIV replication via a novel, non-cytolytic inhibitory mechanism. As will be appreciated by one skilled in the art, however, the systems and assays of the present invention can be used to characterize compounds that suppress or inhibit HIV by both cytolytic and non-cytolytic mechanisms.

Single Cycle HIV Infection Assay:

Because assays that rely on multiple rounds of HIV replication might confound such studies, a novel $CD8^+$ suppression assay was used to measure a single cycle of HIV infection. The assay system utilizes an envelope-defective luciferase reporter virus (as described by Endres et al., 1996, *Cell* 87:745–756) complemented in trans with the gene for an HIV-1 envelope protein, NL4-3 env. In this system, the reporter gene serves as a surrogate for the expression of early proviral genes. The completion of viral entry, reverse transcription and proviral integration is therefore required for expression of the reporter gene. However, expression of the reporter gene is independent of several later stages in HIV-1 replication, including the expression of late gene products, assembly, maturation and budding.

FIG. 17 illustrates data showing suppression of this pseudotyped reporter virus by $CD8^+$ cells. $CD8^+$ T-cell effectors prepared as described in Subsection 10.1, above, inhibited infection of the pseudotyped reporter virus in a dose dependent manner, whereas $CD8^+$ T-cells from HIV-negative donors did not. To determine when infection had proceeded past the stage or stages which is or are susceptible to the $CD8^+$ suppressive activity, $CD8^+$ T-cells were added to $CD4^+$ enriched T-cells at a ratio of 2 to 1 at various times after exposure of the $CD4^+$ enriched T-cells to the pseudotyped virus (FIG. 18A). Consistent with the data presented in FIG. 17, the addition of pooled $CD8^+$ T-cells from HIV-negative donors had little effect on virus replication at each time point. However, the $CD8^+$ effectors derived from an HIV-positive individual completely inhibited viral replication, even when added as late as six hours post-infection. Even at 24 hours post infection, the $CD8^+$ effector cells conferred a log reduction in virus replication that was 94.3% inhibition of control infection. At 48 hours, the suppression was limited to 77% inhibition of the control infection.

Investigation of Known HIV Inhibitors:

Because $CD8^+$ cells were shown to have the capacity to block viral infection at the late time points shown in FIG. 18A, similar "time of addition" assays were done using the pseudotype reporter virus to compare other, known HIV inhibitors which act at known stages in the virus replication cycle.

First, studies like the one shown in FIG. 18A were conducted using two inhibitors, DP178 and anti-$CD4^+$ monoclonal antibody (mAb), which are known to inhibit viral entry. Specifically, DP178 is an HIV gp41 peptide mimic which blocks cell fusion events necessary for viral entry into $CD4^+$ cells (see Wild et al., 1993, *AIDS Res. Hum. Retroviruses* 9:1051–1053; and U.S. Pat. No. 5,464,933). Likewise, the anti-$CD4^+$ monoclonal antibody used in this study, which is referred to as mAb#19 (Connor et al., 1995, *Virology* 206:935–944) is known to block the binding of HIV gp120 to $CD4^+$ cells.

The results of these experiments is shown in FIG. 18B. When either of these two agents was added along with the virus at time zero, viral replication was completely inhibited. However, if two hours passed between the time of infection and time of addition of the inhibitor, viral infection occurred at levels that were 23–43% of those obtained for controls. Further delaying the addition of these inhibitors until 6 hours after infection allowed infection levels to reach 30–61% of the control values (i.e., infection levels in the absence of any inhibitor). These results are in stark contrast to the complete suppression of virus infection by $CD8^+$ cells added at either two or six hours after infection (shown in FIG. 18A), and suggest that HIV-1 entry processes are largely completed within six hours of virus exposure.

Time of addition experiments were also done using nevirapine, a non-nucleoside reverse transcription inhibitor. As can be seen in FIG. 19, however, if nevirapine is added as late as 10 hours post infection, viral infection levels are as high as 67% of control levels. Viral infection levels increase to 85% of control levels if nevirapine is not introduced to the $CD4^+$ cells until 14 hours after virus exposure, suggesting that the process of reverse transcription is complete by 10–14 hours post virus exposure.

Further time of addition experiments were done using an inhibitor of tat described by Hsu et al., 1991, *Science* 254:1799–1802. The tat gene acts at the level of transcriptional activation. Thus, an HIV inhibitor which targets tat acts during the stages of transcription and early proviral gene expression. Addition of the tat inhibitor any time from zero to 24 hours post infection significantly inhibited viral replication. Indeed, and as shown in FIG. 19, addition of the tat inhibitor as late as 24 hours post viral exposure resulted in viral replication levels that are only 46% of control levels.

Finally, a time of addition experiment was performed using nelfinavir, a protease inhibitor, as a negative control. As seen in FIG. 19, however, the protease inhibitor was ineffectual at all time points. This result is not surprising, since protease activity normally occurs at a later stage of the virus replication cycle during virus assembly. Thus, this experiment actually confirmed that the novel pseudotyped reporter virus used here reliably detects only inhibitors that target early stages of HIV replication (e.g., during viral entry, reverse transcription and proviral integration).

The results from these experiments suggest, therefore, that the target (or targets) inhibited by the $CD8^+$ suppressor molecule is (or are) one(s) which is (or are) active during stages of the pseudotyped virus life cycle subsequent to viral entry. Primary targets include, but are not limited to, integration of viral DNA, transactivation from the proviral state, export of tat and/or rev into the cytoplasm and then back into the nucleus, and/or tat mediated enhancement of transcription.

11. DEPOSIT OF MICROORGANISMS AND REFERENCES CITED

Deposit of Microorganisms

The following microorganisms have been deposited with the American Type Culture Collection, (ATCC), 10801 University Boulevard, Manassas, Va. 20110-2209 on the dates indicated below and in compliance with the Budapest Treaty on the International Recognition of the Deposit of Microorganisms for the Purpose of Patent Procedure. The deposited microorganisms have been assigned the following accession numbers:

| Microorganism | Date of Deposit | Accession No. |
| --- | --- | --- |
| DU. HL-2 | March 26, 1993 | CRL 11310 |
| DU. HL-4 | March 26, 1993 | CRL 11309 |
| DU. WS-1-CD8(HVS) | June 5, 1995 | CRL 11919 |
| DU.JR-HVS | March 14, 2000 | PTA-1551 |
| DU.HS-HVS | March 14, 2000 | PTA-1552 |

REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled. Indeed, various modifications of the invention in addition to those described herein will become apparent to those skilled in the art from the foregoing description and accompanying drawings. Such modifications are intended to fall within the scope of the appended claims.

Thus, for example, the present invention is not to be limited in scope by the exemplified embodiments which are intended as illustrations of single aspects of the invention, and any clones, DNA or amino acid sequences which are functionally equivalent are within the scope of the invention. The present invention is also not to be limited in scope by the microorganisms deposited as recited hereinabove, since the deposited embodiments are intended as illustrations of single aspects of the invention. Any microorganisms which are functionally equivalent are therefore within the scope of the invention. It is also to be understood that all base pair sizes given for nucleotides are approximate and are used for purposes of description.

The present invention provides a method for detecting a $CD8^+$ suppressor molecule that has anti-HIV activity, the method comprising contacting a host cell with a replication deficient HIV pseudotyped virus comprising a reporter gene operatively associated with an HIV promoter; contacting the host cell with a sample comprising enriched $CD8^+$ cells or a cell culture of $CD8^+$ cells; and measuring inhibition of reporter gene activity, wherein inhibition of reporter gene activity correlates with anti-HIV activity.

In a further embodiment, the reporter gene is expressed during early proviral gene expression. In another embodiment, the reporter gene is expressed in place of an early proviral gene. In another embodiment, the early proviral gene is a nef gene. In another embodiment, the pseudotyped virus is an env deficient pseudotyped virus. In a further embodiment, the pseudotyped virus is produced by a method which comprises co-transfecting DNA for said pseudotyped virus with a vector that encodes a viral envelope protein. In another further embodiment, the viral envelope protein is an HIV Env protein. In another further embodiment, the viral envelope protein is a non-HIV viral envelope protein.

In other embodiments, the reporter gene is a luciferase gene, a chloramphenicol acetyltransferase gene, a human growth hormone gene or a green fluorescent protein gene.

The present invention also provides a method for detecting a $CD8^+$ suppressor molecule that has anti-HIV activity, the method comprising contacting a host cell with an env deficient HIV pseudotyped virus, comprising a reporter gene substituted for an HIV nef gene, such that said reporter gene is expressed in place of the HIV nef gene; contacting the host cell with a sample comprising (i) enriched $CD8^+$ cells, (ii) a cell culture of $CD8^+$ cells, or (iii) an extract or media component therefrom; and (c) measuring inhibition of reporter gene activity, wherein inhibition of reporter gene activity correlates with anti-HIV activity.

In further embodiments, the reporter gene is a luciferase gene, a chloramphenicol acetyltransferase gene, a human growth hormone gene or a green fluorescent protein gene.

The present invention also provides a diagnostic assay for monitoring clinical progression of HIV infection, said diagnostic assay comprising contacting a host cell with a replication deficient HIV pseudotyped virus comprising a reporter gene operatively associated with an HIV promoter; contacting the host cell with samples from an HIV infected individual, said samples being collected successively from said individual; and measuring inhibition of reporter gene activity when each successive sample is contacted to the host cell, wherein a decrease in the inhibition of reporter gene activity when each successive sample is contacted to the host cell indicates progression of HIV infection.

In a further embodiment, the reporter gene is expressed during early proviral gene expression. In another embodiment, the reporter gene is expressed in place of an early proviral gene. In another embodiment, the early proviral gene is a nef gene. In another embodiment, the pseudotyped virus is an env deficient pseudotyped virus. In a further embodiment, the pseudotyped virus is produced by a method which comprises co-transfecting DNA for said pseudotyped virus with a vector that encodes a viral envelope protein. In another further embodiment, the viral envelope protein is an HIV Env protein. In another further embodiment, the viral envelope protein is a non-HIV viral envelope protein.

In other further embodiments, the reporter gene is a luciferase gene, a chloramphenicol acetyltransferase gene, a human growth hormone gene or a green fluorescent protein gene.

The present invention also provides a diagnostic assay for monitoring clinical progression of HIV infection, said diagnostic assay comprising contacting a host cell with an env deficient HIV pseudotyped virus comprising a reporter gene substituted for an HIV nef gene such that said reporter gene is expressed in place of the HIV nef gene; contacting the host cell with samples from an HIV infection individual, said samples being collected successively from said individual; and measuring inhibition of reporter gene activity when each successive sample is contacted to the host cell, wherein a decrease in the inhibition of reporter gene activity when each successive sample is contacted to the host cell indicates progression of HIV infection.

In further embodiments, the reporter gene is a luciferase gene, a chloramphenicol acetyltransferase gene, a human growth hormone gene or a green fluorescent protein gene.

The present invention also provides a method for detecting a compound that inhibits HIV replication after a particular stage of replication, said method comprising contacting a host cell with a replication deficient HIV pseudotyped virus comprising a reporter gene operatively associated with an HIV promoter; contacting the host cell with a test compound at successive time intervals; and measuring reporter activity at each of said successive time intervals, wherein inhibition of reporter activity at a time interval after the particular stage of replication indicates that the test compound inhibits HIV replication after said particular stage.

In a further embodiment, the reporter gene is expressed during early proviral gene expression. In another embodiment, the early proviral gene is a nef gene. In another embodiment, the pseudotyped virus is an env deficient pseudotyped virus. In a further embodiment, the pseudotyped virus is produced by a method which comprises co-transfecting DNA for said pseudotyped virus with a vector that encodes a viral envelope protein. In a further embodiment, the particular stage of replication is viral entry.

In another embodiment, the method further comprises contacting a different host cell with said HIV pseudotyped virus; contacting the different host cell with a viral entry inhibitor at successive time intervals; and measuring inhibition of reporter activity at each of said time intervals, wherein those time intervals at which reporter activity is inhibited correspond to time intervals of viral entry. In a further embodiment, the viral entry inhibitor is an anti-fusion peptide. In another embodiment, the anti-fusion peptide is DP107, DP178, T1249 or T649.

In another embodiment, the viral entry inhibitor is an antibody that disrupts the interaction between a $CD4^+$ cell surface receptor and a viral envelope protein. In a further embodiment, the antibody is a monoclonal antibody that specifically binds to the $CD4^+$ receptor. In another embodiment, the particular stage of replication is reverse transcription.

In another embodiment, the method further comprises contacting a different host cell with said HIV pseudotyped virus; contacting the different host cell with a reverse transcription inhibitor at successive time intervals; and measuring inhibition of reporter activity at each of said time intervals, wherein those time intervals at which reporter activity is inhibited correspond to time intervals of reverse transcription.

In a further embodiment, the reverse transcription inhibitor is a non-nucleoside reverse transcriptase inhibitor. In one embodiment, the reverse transcriptase inhibitor is nevirapine. In another embodiment, the particular stage of replication is early virus gene expression.

In another embodiment, the method further comprises contacting a different host cell with said HIV pseudotyped virus; contacting the different host cell with an inhibitor of early virus gene expression at successive time intervals; and measuring inhibition of reporter activity at each of said time intervals, wherein those time intervals at which reporter activity is inhibited correspond to time intervals of early virus gene expression. In a further embodiment, the inhibitor of early virus gene expression is a Tat inhibitor.

The present invention also provides a method for obtaining a preparation containing a $CD8^+$ suppressor molecule, said method comprising collecting conditioned media from cells expressing the $CD8^+$ suppressor molecule; fractionating media components of said conditioned media; and identifying a fraction having $CD8^+$ suppressor activity by a method comprising (i) contacting a host cell with a replication deficient pseudotyped HIV virus comprising a reporter gene operatively associated with an HIV promoter, (ii) contacting the host cell with a fractionated media component of said conditioned media, and (iii) measuring inhibition of reporter activity; wherein inhibition of reporter activity correlates with a fraction containing $CD8^+$ suppressor activity. In a further embodiment, the reporter gene is expressed during early proviral gene expression.

The present invention also provides a method for obtaining a preparation containing a $CD8^+$ suppressor molecule, said method comprising preparing an extract from a cell or cell line expressing the $CD8^+$ suppressor molecule; fractionating components of said extract; and identifying a fraction having $CD8^+$ suppressor activity by a method comprising (i) contacting a host cell with a replication deficient pseudotyped HIV virus comprising a reporter gene operatively associated with an HIV promoter, (ii) contacting the host cell with a fractionated component of said extract, and (iii) measuring inhibition of reporter activity; wherein inhibition of reporter activity correlates with a fraction containing a $CD8^+$ suppressor molecule. In a further embodiment, the reporter gene is expressed during early proviral gene expression.

In one embodiment, the reporter gene is expressed in place of an early proviral gene. In a further embodiment, the early proviral gene is a nef gene.

In another embodiment, the pseudotyped virus is an env deficient pseudotyped virus. In a further embodiment, the pseudotyped virus is produced by a method which comprises co-transfecting DNA for said pseudotyped virus with a vector that encodes a viral envelope protein. In one embodiment, the viral envelope protein is an HIV Env protein. In another embodiment, the viral envelope protein is a non-HIV envelope protein. In another embodiment, the conditioned media or extract is prepared from a lymphocyte cell clone that expresses a $CD8^+$ suppressor molecule that inhibits HIV replication.

The present invention also provides a method for isolating a recombinant cDNA clone encoding a $CD8^+$ suppressor molecule that inhibits HIV replication, said method comprising constructing a cDNA expression library using mRNA prepared from $CD8^+$ T-lymphocytes that express a $CD8^+$ suppressor molecule; and screening cDNA products from said cDNA expression library using a method comprising, for each of said cDNA products, (i) contacting a host cell with a replication deficient HIV pseudotyped virus comprising a reporter gene operatively associated with an HIV promoter, (ii) contacting the host cell with a sample comprising a cDNA product from the cDNA expression library, and (iii) measuring inhibition of reporter gene activity; wherein inhibition of reporter gene activity indicates that a recombinant cDNA clone encodes a suppressor molecule that inhibits HIV.

In a further embodiment, the reporter gene is expressed during early proviral gene expression. In another embodiment, the reporter gene is expressed in place of an early proviral gene. In another embodiment, the early proviral gene is a nef gene. In another embodiment, the pseudotyped virus is an env deficient pseudotyped virus. In a further embodiment, the pseudotyped virus is produced by a method which comprises co-transfecting DNA for said pseudotyped virus with a vector that encodes a viral envelope protein. In another further embodiment, the viral envelope protein is an HIV Env protein. In another further embodiment, the viral envelope protein is a non-HIV envelope protein.

In another embodiment, the method further comprises, before said screening step, a step of enriching the cDNA library by eliminating clones that hybridize to cDNAs prepared from mRNA of lymphocytes that do not express a $CD8^+$ suppressor molecule.

The present invention also provides a permanently established lymphocyte cell line that expresses a $CD8^+$ protein on the cell surface and expresses a $CD8^+$ suppressor molecule that inhibits HIV replication, wherein said $CD8^+$ suppressor molecule is a non-cytolytic molecule. In one embodiment, the cell line is the cell line identified as DU.JR-HVS (ATCC Accession No. PTA-1551). In another embodiment, the cell line is the cell line identified as DU.HS-HVS (ATCC Accession No. PTA-1552).

What is claimed is:

1. A method for identifying a $CD8^+$ suppressor molecule that has anti-HIV-1 activity, the method comprising:
   (a) contacting a host cell with a replication deficient HIV pseudotyped virus comprising a reporter gene operatively associated with an HIV promoter;
   (b) contacting the host cell with
      (i) a sample comprising enriched $CD8^+$ cells, or
      (ii) a sample comprising a cell culture of $CD8^+$ cells, or
      (iii) an extract or media component from (i) or (ii), or fraction thereof, or
      (iv) a sample containing a recombinant product expressed from a cDNA library obtained from a $CD8^+$ suppressor cell producing a $CD8^+$ suppressor molecule; and
   (c) measuring reporter gene activity,
   wherein the reporter gene is expressed during early proviral gene expression; and
   wherein inhibition of reporter gene activity during a stage or stages of the pseudotyped viral replication cycle subsequent to viral entry, including but not later than the stage of early proviral gene expression, identifies the presence of a $CD8^+$ suppressor molecule that has anti-HIV-1 activity.

2. The method of claim 1, wherein the inhibition of reporter gene activity occurs during a stage or stages selected from the group consisting of: integration of viral DNA, transactivation from a proviral state, export of tat into the host cell cytoplasm, transport of tat into the host cell nucleus, export of rev into the host cell cytoplasm, transport of rev into the host cell nucleus, tat-mediated enhancement of transcription, reverse transcription, and early gene expression.

3. The method of claim 1, wherein the reporter gene is expressed in place of an early proviral gene.

4. The method of claim 3, wherein the early proviral gene is a nef gene.

5. The method of claim 1, wherein the pseudotyped virus is an env deficient pseudotyped virus.

6. The method of claim 5, wherein the pseudotyped virus is produced by a method comprising co-transfecting DNA for the pseudotyped virus with a vector that encodes a viral envelope protein.

7. The method of claim 6, wherein the viral envelope protein is an HIV Env protein.

8. The method of claim 6, wherein the viral envelope protein is a non-HIV viral envelope protein.

9. The method of claim 1, wherein the reporter gene is a luciferase gene, a chloramphenicol acetyltransferase gene, a growth hormone gene, or a fluorescent protein gene.

10. The method of claim 9, wherein the reporter gene is a luciferase gene.

11. A method for detecting a $CD8^+$ suppressor molecule that has anti-HIV-1 activity, said method comprising:
  (a) contacting a host cell with an Env deficient HIV pseudotyped virus comprising a reporter gene substituted for an HIV nef gene such that said reporter gene is expressed in place of the HIV nef gene;
  (b) contacting the host cell with
    (i) a sample comprising enriched $CD8^+$ cells, or
    (ii) a sample comprising a cell culture of $CD8^+$ cells, or
    (iii) an extract or media component from (i) or (ii), or fraction thereof, or
    (iv) a sample containing a recombinant product expressed from a cDNA library obtained from a $CD8^+$ suppressor cell producting a $CD8^+$ suppressor molecule; and
  (c) measuring reporter gene activity,
  wherein the reporter gene is expressed during early proviral gene expression; and
  wherein inhibition of reporter gene activity during a stage or stages of the pseudotyped viral replication cycle subsequent to viral entry, including but not later than early proviral gene expression, identifies the presence of a $CD8^+$ suppressor molecule that has anti-HIV-1 activity.

12. The method of claim 11, wherein the reporter gene is a luciferase gene, a chloramphenicol acetyltransferase gene, a growth hormone gene, or a fluorescent protein gene.

13. The method of claim 12, wherein the reporter gene is a luciferase gene.

14. The method of claim 11, wherein the inhibition of reporter gene activity occurs during the stage or stages of the virus life cycle selected from the group consisting of: integration of viral DNA, transactivation from a proviral state, export of tat into the host cell cytoplasm, transport of tat into the host cell nucleus, export of rev into the host cell cytoplasm, transport of rev into the host cell nucleus, tat-mediated enhancement of transcription, reverse transcription, and early gene expression.

15. The method of any one of claims 1–13 and 14 wherein step (b) and step (c) are performed at one or more time intervals within 48 hours following step (a), wherein the one or more time intervals corresponds to one or more stages of the HIV pseudotyped virus life cycle, and wherein inhibition of reporter gene activity during a stage of the virus life cycle indicates antiviral activity of the $CD8^+$ suppressor molecule in the stage.

16. The method of claim 15 wherein the inhibition of reporter gene activity occurs during the stage or stages of the virus life cycle selected from the group consisting of: integration of viral DNA, transactivation from a proviral state, export of tat into the host cell cytoplasm, transport of tat into the host cell nucleus, export of rev into the host cell cytoplasm, transport of rev into the host cell nucleus, tat-mediated enhancement of transcription, and reverse transcription.

* * * * *